US011478465B2

(12) United States Patent
Eriksson et al.

(10) Patent No.: US 11,478,465 B2
(45) Date of Patent: Oct. 25, 2022

(54) COMPOUNDS FOR TREATMENT OF EYE DISEASES ASSOCIATED WITH EXCESSIVE VASCULARISATION

(71) Applicant: Active Biotech AB, Lund (SE)

(72) Inventors: Helena Eriksson, Torna Hällestad (SE); Joel Kaye, Netanya (IL); Marie Törngren, Genarp (SE)

(73) Assignee: Active Biotech AB, Lund (SE)

( * ) Notice: Subject to any disclaimer, the term of this patent is extended or adjusted under 35 U.S.C. 154(b) by 0 days.

(21) Appl. No.: 17/366,979

(22) Filed: Jul. 2, 2021

(65) Prior Publication Data

US 2021/0322400 A1 Oct. 21, 2021

Related U.S. Application Data

(63) Continuation of application No. PCT/EP2020/086993, filed on Dec. 18, 2020.

(30) Foreign Application Priority Data

Dec. 19, 2019 (EP) ..................................... 19218062
Feb. 7, 2020 (EP) ..................................... 20156158

(51) Int. Cl.
*A61K 31/4704* (2006.01)
*A61K 47/68* (2017.01)
*A61P 27/02* (2006.01)
*A61K 38/17* (2006.01)
*A61K 39/395* (2006.01)
*C07K 16/22* (2006.01)
*C07K 14/705* (2006.01)

(52) U.S. Cl.
CPC ........ *A61K 31/4704* (2013.01); *A61K 38/179* (2013.01); *A61K 39/3955* (2013.01); *A61K 47/6811* (2017.08); *A61P 27/02* (2018.01); *C07K 16/22* (2013.01); *C07K 14/70503* (2013.01); *C07K 2319/30* (2013.01)

(58) Field of Classification Search
CPC .............. A61K 31/4704; A61K 38/179; A61K 39/3955; A61K 47/6811; A61K 39/395; A61P 27/02; C07K 16/22; C07K 14/70503; C07K 2319/30; C07K 16/00; C07K 2317/24; C07K 2317/76; C07K 2319/32
See application file for complete search history.

(56) References Cited

U.S. PATENT DOCUMENTS

| | | | |
|---|---|---|---|
| 6,077,851 A | 6/2000 | Bjork et al. | |
| 8,580,819 B2 * | 11/2013 | Piryatinsky | A61P 25/00 514/312 |
| 2004/0034227 A1 | 2/2004 | Jansson | |
| 2008/0044444 A1 | 2/2008 | Tamarkin et al. | |
| 2012/0009226 A1 | 1/2012 | Dixit et al. | |
| 2013/0324574 A1 * | 12/2013 | Kaye | A61K 31/4704 514/312 |
| 2016/0213662 A1 * | 7/2016 | Zarnitsyn | A61K 31/4439 |
| 2016/0310417 A1 * | 10/2016 | Prausnitz | A61K 47/38 |
| 2019/0300526 A1 | 10/2019 | Fan et al. | |

FOREIGN PATENT DOCUMENTS

| | | |
|---|---|---|
| EP | 2527344 A1 | 11/2012 |
| WO | 9955678 A1 | 11/1999 |
| WO | 2008124828 A1 | 10/2008 |
| WO | 2012069202 A1 | 5/2012 |
| WO | 2013016684 A1 | 1/2013 |
| WO | 2015060812 A1 | 4/2015 |
| WO | 2017120355 A1 | 7/2017 |
| WO | 2019126424 A1 | 6/2019 |
| WO | 2019126431 A1 | 6/2019 |
| WO | 2019195159 A1 | 10/2019 |

OTHER PUBLICATIONS

He et al., Scientific Reports 11: 10447 (Year: 2021).*
Abdel-Rahman et al., "Investigation of the potential utility of a linomide analogue for treatment of choridal neovascularization". Experimental Eye Research, vol. 91, No. 6, pp. 837-843 (Dec. 1, 2010).
Al-Shabrawey et al., "Targeting Neovascularization in Ischemic Retinopathy: Recent Advances", Expert Rev. Ophthalmol. Jun. 2013; 8(3): 267-286.
Ding et al., "Microglia enhanced the angiogenesis, migration and proliferation of co-cultured RMECs", BMC Ophthalmology,18(1):249 (2018) (12 pages).
Ji Cho et al., "Oxidative stress-mediated TXNIP loss causes RPE dysfunction", Exp Mol Med., 51(10), pp. 1-13 (Oct. 15, 2019).
Li et al., "Laquinimod Inhibits Inflammation-Induced Angiogenesis in the Cornea", Frontiers in Medicine, 7:598056 (Nov. 10, 2020) (12 pages).
Press Release Feb. 5, 2020—Active Biotech announces new strategic direction (4 pages).
Wu et al., "Corneal angiogenesis and lymphangiogenesis", Ocular Disease Mechanisms and Management (2010): 74-82.
Zudaire et al., "A Computational Tool for Quantitative Analysis of Vascular Networks", PLoS One, 6(11), e27385 (Nov. 2011) (12 pages).

* cited by examiner

*Primary Examiner* — Phuong Huynh
(74) *Attorney, Agent, or Firm* — McNeill Baur PLLC

(57) ABSTRACT

The present invention relates to compounds for treatment of a disease or disorder associated with excessive vascularisation of the eye, such as for instance corneal neovascularisation, neovascularisation of the iris, neovascularisation of the ciliary body, corneal pannus, choroidal neovascularisation, retinal neovascularisation, wet age-related macular degeneration, proliferative diabetic retinopathy, retinopathy of prematurity, and ischemic retinopathy.

15 Claims, 2 Drawing Sheets

COMPOUNDS FOR TREATMENT OF EYE DISEASES ASSOCIATED WITH EXCESSIVE VASCULARISATION

CROSS REFERENCE TO RELATED APPLICATIONS

This application is a Continuation of International Application No. PCT/EP2020/086993, filed Dec. 18, 2020, which claims priority to European Application No. 19218062.8, filed Dec. 19, 2019, and European Application No. 20156158.6, Feb. 7, 2020, each of which is incorporated by reference herein in its entirety for all purposes.

TECHNICAL FIELD

The present invention relates to compounds and compositions for treatment of a disease or disorder associated with excessive vascularisation of the eye, such as for instance corneal neovascularisation, neovascularisation of the iris, neovascularisation of the ciliary body, corneal pannus, choroidal neovascularisation, retinal neovascularisation, wet age-related macular degeneration, proliferative diabetic retinopathy, retinopathy of prematurity, and ischemic retinopathy.

BACKGROUND

Laquinimod and Tasquinimod

Laquinimod and tasquinimod, second generation quinoline-3-carboxamide compounds, have been developed as oral immunomodulators intended for the treatment of relapsing multiple sclerosis (MS) and metastatic chemo naïve prostate cancer (mCRPC), respectively.

Efficacy and safety of laquinimod have been assessed in clinical Phase 1-3 studies, and it has a well-established clinical safety profile based on over 14000 patient years of exposure to daily doses of up to 0.6 mg in relapsing MS patients. The data from the clinical development program in MS have demonstrated a consistent clinical benefit on annual relapse rate, the widely used endpoint in relapsing MS. Laquinimod treatment also results in certain disability progression indicators.

Efficacy and safety of tasquinimod has been assessed in global randomized placebo controlled Phase 2 and 3 studies. Disease progression (primary endpoint) was significantly delayed by tasquinimod treatment in the Phase 2 and 3 studies.

Eye Disorders

Many eye diseases and disorders have no early symptoms. They may be painless, and the patient may see no change in their vision until the disease has become quite advanced. Therefore, prevention, treatment, and/or delaying progression of such diseases or disorders is paramount.

Age-related Macular Degeneration (AMD) is a devastating disease affecting individuals of over 60 years of age. It is the leading cause of irreversible, severe visual loss in the developed world. The disease results in damaging sharp and central vision. Central vision is needed for seeing objects clearly and for common daily tasks such as reading and driving. AMD affects the macula, the central part the retina that allows the eye to see fine details. There are two forms of AMD-wet and dry.

Dry AMD is when the macula thins overtime as part of aging process, gradually blurring central vision. The dry form is more common and accounts for 70-90% of cases of AMD and it progresses more slowly than the wet form. Over time, as less of the macula functions, central vision is gradually lost in the affected eye. Dry AMD generally affects both eyes. One of the most common early signs of dry AMD is drusen.

The exudative ("wet"), or neovascular form of AMD—wet AMD—causes vision loss due to abnormal blood vessel growth (choroidal neovascularization) in the choriocapillaris, through Bruch's membrane, ultimately leading to blood and protein leakage below the macula. Bleeding, leaking, and scarring from these blood vessels may lead to detachment of the retinal pigment epithelium and irreversible damage to the photoreceptors and rapid vision loss if left untreated.

SUMMARY

As described above, a treatment for an eye disease or eye disorder associated with excessive vascularisation such as wet age-related macular degeneration is highly desired. Such a treatment could potentially prevent or reduce damage to eye tissues, such as the macula, which would severely improve the prognosis for subjects suffering from such eye diseases or eye disorders.

The present disclosure relates to a composition comprising a compound of formula (I) for use in the treatment of an eye disease or eye disorder associated with excessive vascularisation of the eye. The inventors of the present disclosure have surprisingly found that treatment of induced vascularisation of eye tissues resulted in reduced vascularisation of either cornea or choroid. More specifically, the inventors have surprisingly found that compositions comprising compounds of the invention suppress choroidal neovascularisation in a laser-induced choroidal neovascularisation rat model. The inventors have also found a surprising effect in the treatment growth-factor-stimulated neovascularisation in a mouse model, where compositions comprising compounds of the invention were capable of reducing the area of vascularisation. These findings enable a complete new way to address the treatment of diseases and disorders associated with excessive vascularisation of the eye, which could potentially lead to better prognosis for patients sufferings from diseases such as corneal neovascularisation, neovascularisation of the iris, neovascularisation of the ciliary body, corneal pannus, choroidal neovascularisation, retinal neovascularisation, wet age-related macular degeneration, proliferative diabetic retinopathy, retinopathy of prematurity, and ischemic retinopathy.

The present disclosure thus provides a composition comprising a compound according to any one of formulas (I) to (IX) for use in treatment of an eye disease or eye disorder.

One aspect of the disclosure provides for a composition comprising a compound according to formula (IX):

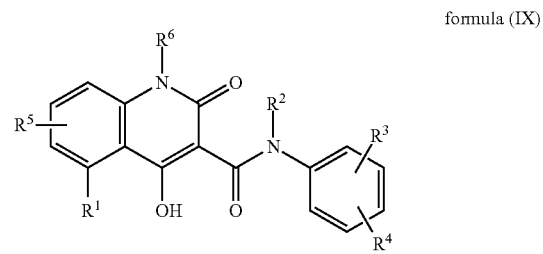

formula (IX)

wherein
R¹ is selected from the group consisting of hydrogen, hydroxy, methyl, ethyl, n-propyl, iso-propyl, methoxy, ethoxy, fluoro, chloro, bromo, trifluoromethyl, and trifluoromethoxy, R² is selected from the group consisting of hydrogen and C1-C4 alkyl, such as methyl, ethyl, or vinyl, R³ is selected from the group consisting of hydrogen, hydroxy, methyl, methoxy, fluoro, chloro, bromo, trifluoromethyl, and trifluoromethoxy, R⁴ is selected from the group consisting of hydrogen, fluoro and chloro, with the proviso that R⁴ is selected from fluoro and chloro only when R³ is selected from fluoro and chloro, R⁵ is hydrogen or hydroxy, and
R⁶ is methyl or hydrogen,
or a pharmaceutically acceptable salt thereof, for use in the treatment of an eye disease or eye disorder.

In one aspect, a composition comprising a compound of formula (I) is provided:

formula (I)

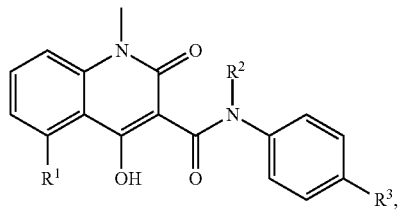

wherein:
R¹ is chloro, R² is ethyl, and R³ is hydrogen,
R¹ is methoxy, R² is methyl, and R³ is trifluoromethyl,
R¹ is chloro, R² is hydrogen, and R³ is hydrogen,
or
R¹ is methoxy, R² is hydrogen, and R³ is trifluoromethyl;
or a pharmaceutically acceptable salt thereof, for use in the treatment of an eye disease or eye disorder.

One specific aspect of the disclosure provides for a composition comprising a compound of formula (II), formula (III), formula (IV), or formula (V) is provided:

formula (II)

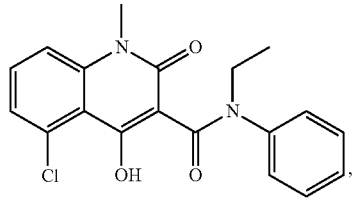

formula (III)

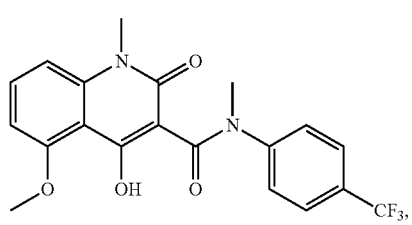

formula (IV)

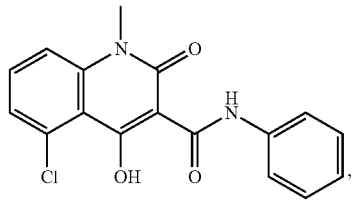

formula (V)

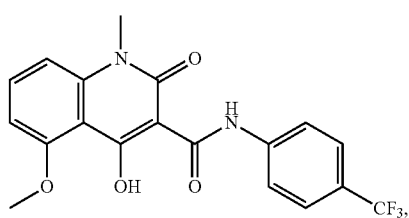

or a pharmaceutically acceptable salt thereof, for use in the treatment of an eye disease or eye disorder.

A specific aspect of the present disclosure provides for a composition comprising a compound selected from the group consisting of:

laquinimod,
5-chloro-N-ethyl-4-hydroxy-N-(4-hydroxyphenyl)-1-methyl-2-oxo-1,2-dihydroquinoline-3-carboxamide,
5-chloro-4-hydroxy-1-methyl-2-oxo-N-phenyl-1,2-dihydroquinoline-3-carboxamide,
5-chloro-N-ethyl-4-hydroxy-2-oxo-N-phenyl-1,2-dihydroquinoline-3-carboxamide,
5-chloro-N-ethyl-4,8-dihydroxy-1-methyl-2-oxo-N-phenyl-1,2-dihydroquinoline-3-carboxamide,
5-chloro-N-ethyl-4,7-dihydroxy-1-methyl-2-oxo-N-phenyl-1,2-dihydroquinoline-3-carboxamide,
5-chloro-N-ethyl-4,6-dihydroxy-1-methyl-2-oxo-N-phenyl-1,2-dihydroquinoline-3-carboxamide,
5-chloro-4-hydroxy-1-methyl-2-oxo-N-phenyl-N-vinyl-1,2-dihydroquinoline-3-carboxamide,
5-chloro-N-ethyl-4-hydroxy-N-(4-hydroxyphenyl)-1-methyl-2-oxo-1,2-dihydroquinoline-3-carboxamide,
N-ethyl-4-hydroxy-1-methyl-2-oxo-N-phenyl-1,2-dihydroquinoline-3-carboxamide,
5'-chloro-1-ethyl-1'-methyl-2'H-spiro[indoline-3,3'-quinoline]-2,2',4'(1'H)-trione,
tasquinimod,
4-hydroxy-5-methoxy-N-methyl-2-oxo-N-(4-(trifluoromethyl)phenyl)-1,2-dihydroquinoline-3-carboxamide,
4,5-dihydroxy-N,1-dimethyl-2-oxo-N-(4-(trifluoromethyl)phenyl)-1,2-dihydroquinoline-3-carboxamide,
4-hydroxy-5-methoxy-1-methyl-2-oxo-N-(4-(trifluoromethyl)phenyl)-1,2-dihydroquinoline-3-carboxamide,
4,6-dihydroxy-5-methoxy-N,1-dimethyl-2-oxo-N-(4-(trifluoromethyl)phenyl)-1,2-dihydroquinoline-3-carboxamide,
4,7-dihydroxy-5-methoxy-N,1-dimethyl-2-oxo-N-(4-(trifluoromethyl)phenyl)-1,2-dihydroquinoline-3-carboxamide, and
4,8-dihydroxy-5-methoxy-N,1-dimethyl-2-oxo-N-(4-(trifluoromethyl)phenyl)-1,2-dihydroquinoline-3-carboxamide, or a pharmaceutically acceptable salt thereof, for use in the treatment of an eye disease or eye disorder.

One aspect of the disclosure provides for a method of treating an eye disease or eye disorder, wherein said method comprises administering a composition comprising a compound according to formula (IX):

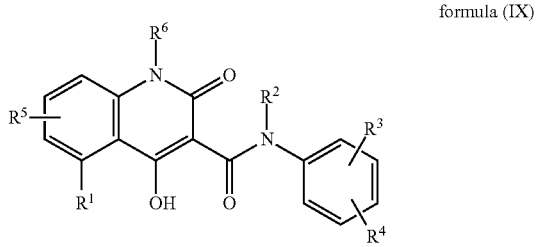
formula (IX)

wherein $R^1$ is selected from the group consisting of hydrogen, hydroxy, methyl, ethyl, n-propyl, iso-propyl, methoxy, ethoxy, fluoro, chloro, bromo, trifluoromethyl, and trifluoromethoxy, $R^2$ is selected from the group consisting of hydrogen and C1-C4 alkyl, such as methyl, ethyl, or vinyl, $R^3$ is selected from the group consisting of hydrogen, hydroxy, methyl, methoxy, fluoro, chloro, bromo, trifluoromethyl, and trifluoromethoxy, $R^4$ is selected from the group consisting of hydrogen, fluoro and chloro, with the proviso that $R^4$ is selected from fluoro and chloro only when $R^3$ is selected from fluoro and chloro, $R^5$ is hydrogen or hydroxy, and $R^6$ is methyl or hydrogen, or a pharmaceutically acceptable salt thereof.

One aspect of the disclosure provides for a use of a compound according to formula (IX):

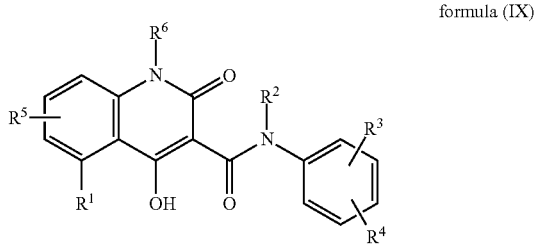
formula (IX)

wherein $R^1$ is selected from the group consisting of hydrogen, hydroxy, methyl, ethyl, n-propyl, iso-propyl, methoxy, ethoxy, fluoro, chloro, bromo, trifluoromethyl, and trifluoromethoxy, $R^2$ is selected from the group consisting of hydrogen and C1-C4 alkyl, such as methyl, ethyl, or vinyl, $R^3$ is selected from the group consisting of hydrogen, hydroxy, methyl, methoxy, fluoro, chloro, bromo, trifluoromethyl, and trifluoromethoxy, $R^4$ is selected from the group consisting of hydrogen, fluoro and chloro, with the proviso that $R^4$ is selected from fluoro and chloro only when $R^3$ is selected from fluoro and chloro, $R^5$ is hydrogen or hydroxy, and $R^6$ is methyl or hydrogen, or a pharmaceutically acceptable salt thereof, for the manufacture of a medicament for the treatment of an eye disease or eye disorder.

DETAILED DESCRIPTION

Definitions

Figure 1:
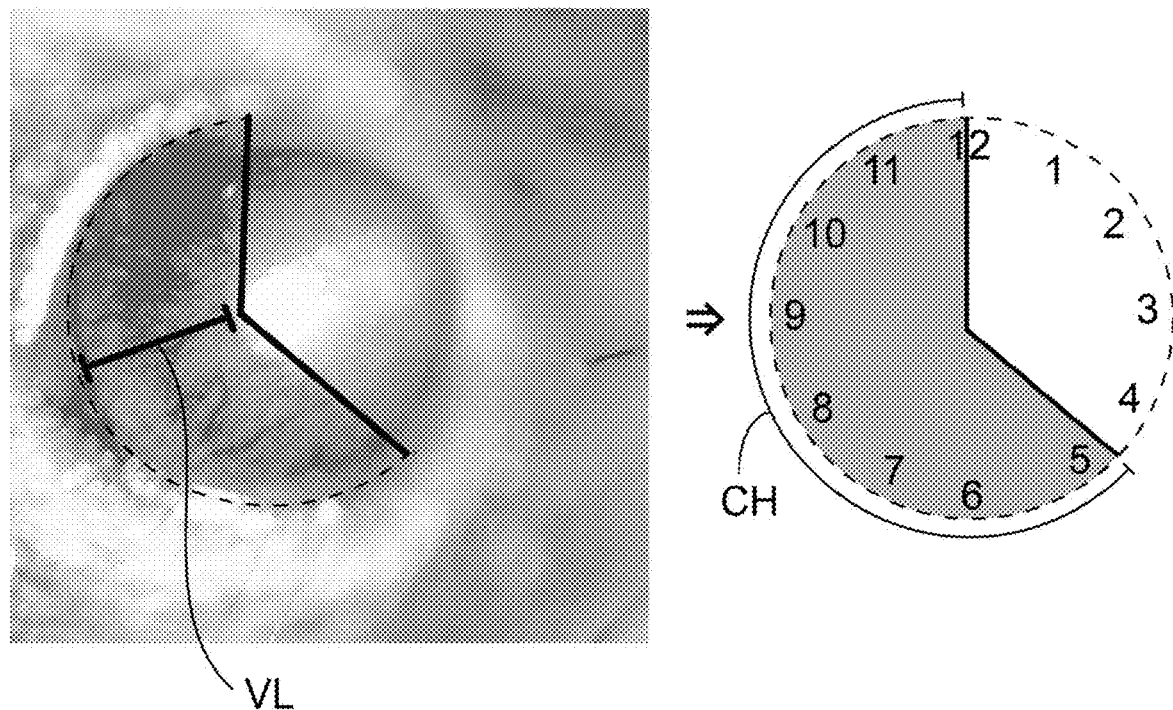
FIG. 1: Photography of mouse eye with clearly visible vascularisation. The overlaid graphic illustrates how to measure the average vessel length (VL) from limbal vessels toward the pellet and continuous circumferential zone (in clock hours=CH).

By the term "C1-C4 alkyl" is meant a moiety comprising or consisting of one, two, three, or four carbon atoms and a number of hydrogen atoms. Examples of C1-C4 alkyl groups are methyl, ethyl, vinyl, isopropyl, n-propyl, n-butyl, tert-butyl, iso-butyl, or sec-butyl.

By "laquinimod" or "ABR-215062" is meant a chemical compound of formula (II):

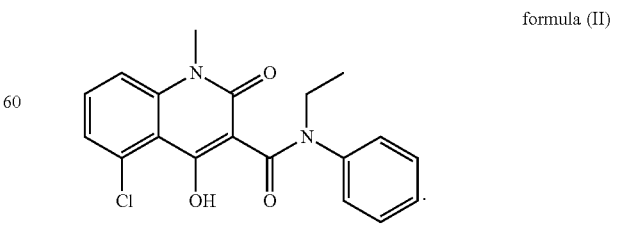
formula (II)

By "tasquinimod" is meant a chemical compound of formula (III):

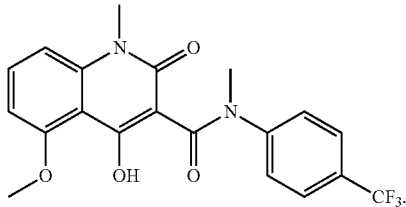

formula (III)

By "ABR-215174" is meant 5-chloro-4-hydroxy-1-methyl-2-oxo-1,2-dihydroquinoline-3-carboxylic acid phenylamide, i.e. a compound of formula (IV):

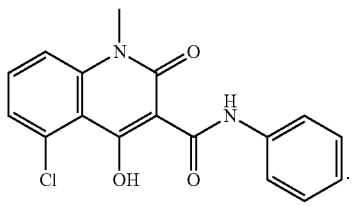

formula (IV)

By "ABR-215691" is meant 4-hydroxy-5-methoxy-1-methyl-2-oxo-N-(4-(trifluoromethyl)phenyl)-1,2-dihydroquinoline-3-carboxamide, i.e. a compound of formula (V):

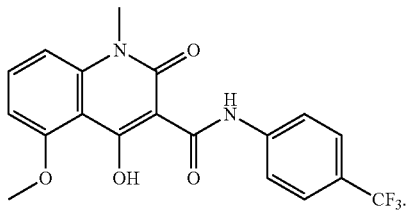

formula (V)

By "vascularisation" and "neovascularisation" is meant a process by which new blood vessels form. "vascularisation" and "neovascularisation" are used interchangeably herein.

As used herein, "vascularisation of the eye" is synonymous to ocular neovascularisation.

By "excessive vascularisation" is meant an event wherein vascularisation occurs to an extent that is deleterious to the normal functioning of the affected tissue. Such excessive vascularisation occurs during or as an effect of eye diseases or eye disorders such as corneal neovascularisation, neovascularisation of the iris, neovascularisation of the ciliary body, corneal pannus, choroidal neovascularisation, proliferative diabetic retinopathy, retinopathy of prematurity, ischemic retinopathy, retinal neovascularisation, and wet age-related macular degeneration.

In the context of the present disclosure, the terms "an eye disease or eye disorder associated with excessive vascularisation of the eye" and "an eye disease or eye disorder associated with vascularisation of the eye" are taken to mean any eye disease or eye disorder which is considered by those of skill in the art to be caused by, and/or effect vascularisation of one or more tissues of the eye, e.g. in which said vascularisation is deleterious to the normal functioning of the affected tissue. Such diseases or disorders can lead to loss of vision.

By "treatment" is generally meant to encompass prohibiting, preventing, restraining, and slowing, stopping or reversing progression or severity of an eye disease or eye disorder.

In relation to vascularisation, the term "extent" is taken to mean the severity of the vascularisation. Such extent of vascularisation can be assessed using several different measureable parameters, such as the area of vascularisation, the amount of vessels in the vascularised area, the length of the vessels in the vascularised area, or the thickness of the vessels in the vascularised area.

By "laquinimod vehicle" is meant a vehicle used for laquinimod. The vehicle does not contain laquinimod.

By "VEGF" is meant vascular endothelial growth factor. In mammals, the VEGF family comprises five members, namely VEGF-A, VEGF-B, VEGF-C, VEGF-D, and placental growth factor (PGF). VEGF stimulates cellular responses by binding to the VEGF receptor (VEGFR).

By "bFGF" is meant basic fibroblast growth factor.

Compounds and Compositions for Use

In one embodiment of the present disclosure, a composition comprising a compound of formula (I) is provided:

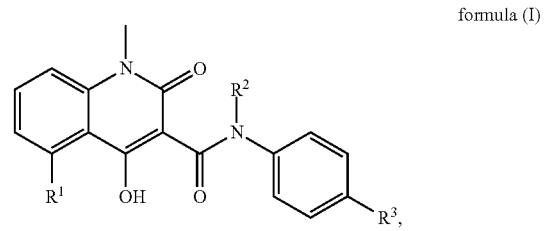

formula (I)

wherein:

$R^1$ is chloro, $R^2$ is ethyl, and $R^3$ is hydrogen, $R^1$ is methoxy, $R^2$ is methyl, and $R^3$ is trifluoromethyl, $R^1$ is chloro, $R^2$ is hydrogen, and $R^3$ is hydrogen, or $R^1$ is methoxy, $R^2$ is hydrogen, and $R^3$ is trifluoromethyl;

or a pharmaceutically acceptable salt thereof, for use in the treatment of an eye disease or eye disorder.

In a further embodiment of the present disclosure, a composition comprising a compound of formula (I) is provided wherein $R^1$ is chloro, $R^2$ is ethyl, and $R^3$ is hydrogen, for use in the treatment of an eye disease or eye disorder. The common name of the compound wherein $R^1$ is Cl, $R^2$ is ethyl, and $R^3$ is H is laquinimod.

In a yet further embodiment of the present disclosure, a composition comprising a compound of formula (I) is provided wherein $R^1$ is methoxy, $R^2$ is methyl, and $R^3$ is trifluoromethyl, for use in the treatment of an eye disease or eye disorder. The common name of the compound wherein $R^1$ is methoxy, $R^2$ is methyl, and $R^3$ is trifluoromethyl is tasquinimod.

In one embodiment, a method for treating an eye disease or eye disorder is provided, said method comprising administering a composition comprising a therapeutically effective amount of a compound according to formula (I):

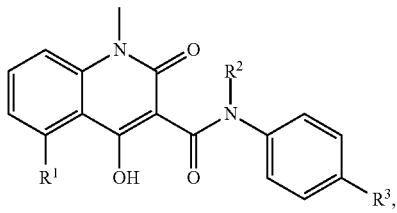

formula (I)

wherein:
$R^1$ is chloro, $R^2$ is ethyl, and $R^3$ is hydrogen,
$R^1$ is methoxy, $R^2$ is methyl, and $R^3$ is trifluoromethyl,
$R^1$ is chloro, $R^2$ is hydrogen, and $R^3$ is hydrogen,
or
$R^1$ is methoxy, $R^2$ is hydrogen, and $R^3$ is trifluoromethyl;
or a pharmaceutically acceptable salt thereof to a subject in need thereof.

In one embodiment, the present disclosure relates to use of a compound according to formula (I),

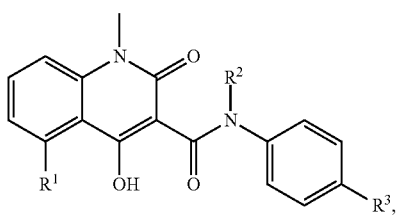

formula (I)

wherein:
$R^1$ is chloro, $R^2$ is ethyl, and $R^3$ is hydrogen,
$R^1$ is methoxy, $R^2$ is methyl, and $R^3$ is trifluoromethyl
$R^1$ is chloro, $R^2$ is hydrogen, and $R^3$ is hydrogen,
or
$R^1$ is methoxy, $R^2$ is hydrogen, and $R^3$ is trifluoromethyl;
or a pharmaceutically acceptable salt thereof for the manufacture of a medicament for the treatment of an eye disease or eye disorder.

Disclosed herein are also metabolites of laquinimod and tasquinimod. Laquinimod and tasquinimod are subject to metabolism upon administration to a subject. Certain metabolites, such as those disclosed herein have therapeutic activity. One embodiment of the disclosure provides for a composition comprising laquinimod, tasquinimod, or an active metabolite thereof, for use in treatment of an eye disease or eye disorder. In one embodiment of the present disclosure, laquinimod or an active metabolite thereof is administered to a subject in need thereof. In another embodiment, tasquinimod or an active metabolite thereof is administered to a subject in need thereof.

Metabolites of laquinimod include those formed by quinoline hydroxylation at various sites, quinoline demethylation, aniline deethylation, and aniline hydroxylation at the para position. Specific examples of metabolites of laquinimod include:
5-chloro-N-ethyl-4-hydroxy-N-(4-hydroxyphenyl)-1-methyl-2-oxo-1,2-dihydroquinoline-3-carboxamide,
5-chloro-4-hydroxy-1-methyl-2-oxo-N-phenyl-1,2-dihydroquinoline-3-carboxamide,
5-chloro-N-ethyl-4-hydroxy-2-oxo-N-phenyl-1,2-dihydroquinoline-3-carboxamide,
5-chloro-N-ethyl-4,8-dihydroxy-1-methyl-2-oxo-N-phenyl-1,2-dihydroquinoline-3-carboxamide,
5-chloro-N-ethyl-4,7-dihydroxy-1-methyl-2-oxo-N-phenyl-1,2-dihydroquinoline-3-carboxamide,
5-chloro-N-ethyl-4,6-dihydroxy-1-methyl-2-oxo-N-phenyl-1,2-dihydroquinoline-3-carboxamide,
5-chloro-4-hydroxy-1-methyl-2-oxo-N-phenyl-N-vinyl-1,2-dihydroquinoline-3-carboxamide,
5-chloro-N-ethyl-4-hydroxy-N-(4-hydroxyphenyl)-1-methyl-2-oxo-1,2-dihydroquinoline-3-carboxamide,
N-ethyl-4-hydroxy-1-methyl-2-oxo-N-phenyl-1,2-dihydroquinoline-3-carboxamide, and
5'-chloro-1-ethyl-1'-methyl-2'H-spiro[indoline-3,3'-quinoline]-2,2',4'(1'H)-trione.

A preferred embodiment of the disclosure provides for the laquinimod metabolite 5-chloro-4-hydroxy-1-methyl-2-oxo-N-phenyl-1,2-dihydroquinoline-3-carboxamide (5-chloro-4-hydroxy-1-methyl-2-oxo-1,2-dihydroquinoline-3-carboxylic acid phenylamide, ABR-215174).

Metabolites of tasquinimod include those formed by aniline demethylation, quinoline-N demethylation, and quinoline-O demethylation. Specific example of tasquinimod metabolites include:
4-hydroxy-5-methoxy-N-methyl-2-oxo-N-(4-(trifluoromethyl)phenyl)-1,2-dihydroquinoline-3-carboxamide,
4,5-dihydroxy-N,1-dimethyl-2-oxo-N-(4-(trifluoromethyl)phenyl)-1,2-dihydroquinoline-3-carboxamide, and
4-hydroxy-5-methoxy-1-methyl-2-oxo-N-(4-(trifluoromethyl)phenyl)-1,2-dihydroquinoline-3-carboxamide,
4,6-dihydroxy-5-methoxy-N,1-dimethyl-2-oxo-N-(4-(trifluoromethyl)phenyl)-1,2-dihydroquinoline-3-carboxamide,
4,7-dihydroxy-5-methoxy-N,1-dimethyl-2-oxo-N-(4-(trifluoromethyl)phenyl)-1,2-dihydroquinoline-3-carboxamide, and
4,8-dihydroxy-5-methoxy-N,1-dimethyl-2-oxo-N-(4-(trifluoromethyl)phenyl)-1,2-dihydroquinoline-3-carboxamide.

A preferred embodiment of the present disclosure provides for the tasquinimod metabolite 4-hydroxy-5-methoxy-1-methyl-2-oxo-N-(4-(trifluoromethyl)phenyl)-1,2-dihydroquinoline-3-carboxamide.

In a preferred embodiment of the present disclosure, the compound is selected from the group consisting of laquinimod, tasquinimod, 5-chloro-4-hydroxy-1-methyl-2-oxo-1,2-dihydroquinoline-3-carboxylic acid phenylamide (compound of formula (IV)) and 4-hydroxy-5-methoxy-1-methyl-2-oxo-N-(4-(trifluoromethyl)phenyl)-1,2-dihydroquinoline-3-carboxamide (compound of formula (V)).

One embodiment of the present disclosure provides for a composition comprising a compound selected from the group consisting of:
laquinimod,
5-chloro-N-ethyl-4-hydroxy-N-(4-hydroxyphenyl)-1-methyl-2-oxo-1,2-dihydroquinoline-3-carboxamide,
5-chloro-4-hydroxy-1-methyl-2-oxo-N-phenyl-1,2-dihydroquinoline-3-carboxamide,
5-chloro-N-ethyl-4-hydroxy-2-oxo-N-phenyl-1,2-dihydroquinoline-3-carboxamide,
5-chloro-N-ethyl-4,8-dihydroxy-1-methyl-2-oxo-N-phenyl-1,2-dihydroquinoline-3-carboxamide,
5-chloro-N-ethyl-4,7-dihydroxy-1-methyl-2-oxo-N-phenyl-1,2-dihydroquinoline-3-carboxamide,
5-chloro-N-ethyl-4,6-dihydroxy-1-methyl-2-oxo-N-phenyl-1,2-dihydroquinoline-3-carboxamide, 5-chloro-4-hydroxy-1-methyl-2-oxo-N-phenyl-N-vinyl-1,2-dihydroquinoline-3-carboxamide,
5-chloro-N-ethyl-4-hydroxy-N-(4-hydroxyphenyl)-1-methyl-2-oxo-1,2-dihydroquinoline-3-carboxamide,
N-ethyl-4-hydroxy-1-methyl-2-oxo-N-phenyl-1,2-dihydroquinoline-3-carboxamide,
5'-chloro-1-ethyl-1'-methyl-2'H-spiro[indoline-3,3'-quinoline]-2,2',4'(1'H)-trione,
tasquinimod,
4-hydroxy-5-methoxy-N-methyl-2-oxo-N-(4-(trifluoromethyl)phenyl)-1,2-dihydroquinoline-3-carboxamide,
4,5-dihydroxy-N,1-dimethyl-2-oxo-N-(4-(trifluoromethyl)phenyl)-1,2-dihydroquinoline-3-carboxamide,
4-hydroxy-5-methoxy-1-methyl-2-oxo-N-(4-(trifluoromethyl)phenyl)-1,2-dihydroquinoline-3-carboxamide,
4,6-dihydroxy-5-methoxy-N,1-dimethyl-2-oxo-N-(4-(trifluoromethyl)phenyl)-1,2-dihydroquinoline-3-carboxamide,
4,7-dihydroxy-5-methoxy-N,1-dimethyl-2-oxo-N-(4-(trifluoromethyl)phenyl)-1,2-dihydroquinoline-3-carboxamide, and
4,8-dihydroxy-5-methoxy-N,1-dimethyl-2-oxo-N-(4-(trifluoromethyl)phenyl)-1,2-dihydroquinoline-3-carboxamide,
or a pharmaceutically acceptable salt thereof, for use in the treatment of an eye disease or eye disorder, wherein said eye disease or eye disorder is associated with excessive vascularisation of the eye.

One embodiment of the present disclosure provides for a method of treating an eye disease or eye disorder is provided, said method comprising administering a composition comprising a therapeutically effective amount of a compound selected from the group consisting of:
laquinimod,
5-chloro-N-ethyl-4-hydroxy-N-(4-hydroxyphenyl)-1-methyl-2-oxo-1,2-dihydroquinoline-3-carboxamide,
5-chloro-4-hydroxy-1-methyl-2-oxo-N-phenyl-1,2-dihydroquinoline-3-carboxamide,
5-chloro-N-ethyl-4-hydroxy-2-oxo-N-phenyl-1,2-dihydroquinoline-3-carboxamide,
5-chloro-N-ethyl-4,8-dihydroxy-1-methyl-2-oxo-N-phenyl-1,2-dihydroquinoline-3-carboxamide,
5-chloro-N-ethyl-4,7-dihydroxy-1-methyl-2-oxo-N-phenyl-1,2-dihydroquinoline-3-carboxamide,
5-chloro-N-ethyl-4,6-dihydroxy-1-methyl-2-oxo-N-phenyl-1,2-dihydroquinoline-3-carboxamide,
5-chloro-4-hydroxy-1-methyl-2-oxo-N-phenyl-N-vinyl-1,2-dihydroquinoline-3-carboxamide,
5-chloro-N-ethyl-4-hydroxy-N-(4-hydroxyphenyl)-1-methyl-2-oxo-1,2-dihydroquinoline-3-carboxamide,
N-ethyl-4-hydroxy-1-methyl-2-oxo-N-phenyl-1,2-dihydroquinoline-3-carboxamide,
5'-chloro-1-ethyl-1'-methyl-2'H-spiro[indoline-3,3'-quinoline]-2,2',4'(1'H)-trione,
tasquinimod,
4-hydroxy-5-methoxy-N-methyl-2-oxo-N-(4-(trifluoromethyl)phenyl)-1,2-dihydroquinoline-3-carboxamide,
4,5-dihydroxy-N,1-dimethyl-2-oxo-N-(4-(trifluoromethyl)phenyl)-1,2-dihydroquinoline-3-carboxamide,
4-hydroxy-5-methoxy-1-methyl-2-oxo-N-(4-(trifluoromethyl)phenyl)-1,2-dihydroquinoline-3-carboxamide,
4,6-dihydroxy-5-methoxy-N,1-dimethyl-2-oxo-N-(4-(trifluoromethyl)phenyl)-1,2-dihydroquinoline-3-carboxamide,
4,7-dihydroxy-5-methoxy-N,1-dimethyl-2-oxo-N-(4-(trifluoromethyl)phenyl)-1,2-dihydroquinoline-3-carboxamide, and
4,8-dihydroxy-5-methoxy-N,1-dimethyl-2-oxo-N-(4-(trifluoromethyl)phenyl)-1,2-dihydroquinoline-3-carboxamide,
or a pharmaceutically acceptable salt thereof to a subject in need thereof.

One embodiment of the present disclosure provides for a use of a compound selected from the group consisting of:
laquinimod,
5-chloro-N-ethyl-4-hydroxy-N-(4-hydroxyphenyl)-1-methyl-2-oxo-1,2-dihydroquinoline-3-carboxamide,
5-chloro-4-hydroxy-1-methyl-2-oxo-N-phenyl-1,2-dihydroquinoline-3-carboxamide,
5-chloro-N-ethyl-4-hydroxy-2-oxo-N-phenyl-1,2-dihydroquinoline-3-carboxamide,
5-chloro-N-ethyl-4,8-dihydroxy-1-methyl-2-oxo-N-phenyl-1,2-dihydroquinoline-3-carboxamide,
5-chloro-N-ethyl-4,7-dihydroxy-1-methyl-2-oxo-N-phenyl-1,2-dihydroquinoline-3-carboxamide,
5-chloro-N-ethyl-4,6-dihydroxy-1-methyl-2-oxo-N-phenyl-1,2-dihydroquinoline-3-carboxamide,
5-chloro-4-hydroxy-1-methyl-2-oxo-N-phenyl-N-vinyl-1,2-dihydroquinoline-3-carboxamide,
5-chloro-N-ethyl-4-hydroxy-N-(4-hydroxyphenyl)-1-methyl-2-oxo-1,2-dihydroquinoline-3-carboxamide,
N-ethyl-4-hydroxy-1-methyl-2-oxo-N-phenyl-1,2-dihydroquinoline-3-carboxamide,
5'-chloro-1-ethyl-1'-methyl-2'H-spiro[indoline-3,3'-quinoline]-2,2',4'(1'H)-trione,
tasquinimod,
4-hydroxy-5-methoxy-N-methyl-2-oxo-N-(4-(trifluoromethyl)phenyl)-1,2-dihydroquinoline-3-carboxamide,
4,5-dihydroxy-N,1-dimethyl-2-oxo-N-(4-(trifluoromethyl)phenyl)-1,2-dihydroquinoline-3-carboxamide,
4-hydroxy-5-methoxy-1-methyl-2-oxo-N-(4-(trifluoromethyl)phenyl)-1,2-dihydroquinoline-3-carboxamide,
4,6-dihydroxy-5-methoxy-N,1-dimethyl-2-oxo-N-(4-(trifluoromethyl)phenyl)-1,2-dihydroquinoline-3-carboxamide,
4,7-dihydroxy-5-methoxy-N,1-dimethyl-2-oxo-N-(4-(trifluoromethyl)phenyl)-1,2-dihydroquinoline-3-carboxamide, and
4,8-dihydroxy-5-methoxy-N,1-dimethyl-2-oxo-N-(4-(trifluoromethyl)phenyl)-1,2-dihydroquinoline-3-carboxamide,
or a pharmaceutically acceptable salt thereof, for the manufacture of a medicament for the treatment of an eye disease or eye disorder.

One embodiment of the present disclosure provides for a composition comprising a compound according to formula (VI):

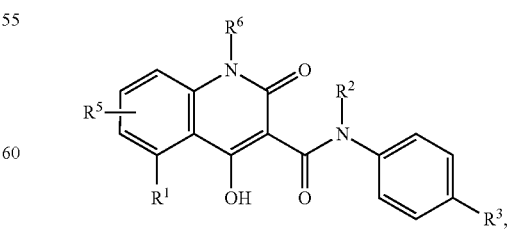

formula (VI)

wherein
$R^1$ is chloro,
$R^2$ is ethyl or hydrogen, $R^3$ is hydrogen or hydroxy,
$R^5$ is hydrogen or hydroxy, and
$R^6$ is methyl or hydrogen
or a pharmaceutically acceptable salt thereof, for use in the treatment of an eye disease or eye disorder.

One embodiment of the present disclosure provides for a composition comprising a compound according to formula (VII):

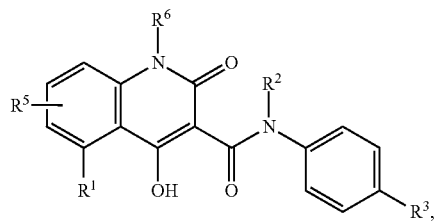

formula (VII)

wherein:
$R^1$ is methoxy or hydroxy,
$R^2$ is methyl or hydrogen,
$R^3$ is trifluoromethyl,
$R^5$ is hydrogen or hydroxy, and
$R^6$ is methyl or hydrogen
or a pharmaceutically acceptable salt thereof, for use in the treatment of an eye disease or eye disorder.

One embodiment of the present disclosure provides for a composition comprising a compound according to formula (VIII):

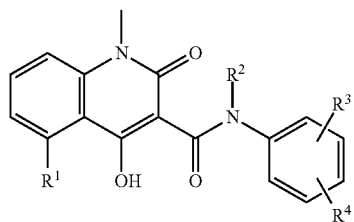

formula (VIII)

wherein
$R^1$ is selected from the group consisting of hydrogen, hydroxy, methyl, ethyl, n-propyl, iso-propyl, methoxy, ethoxy, fluoro, chloro, bromo, trifluoromethyl, and trifluoromethoxy,
$R^2$ is selected from the group consisting of hydrogen and C1-C4 alkyl, such as methyl, ethyl, or vinyl,
$R^3$ is selected from the group consisting of hydrogen, hydroxy, methyl, methoxy, fluoro, chloro, bromo, trifluoromethyl, and trifluoromethoxy, and
$R^4$ is selected from the group consisting of hydrogen, fluoro and chloro, with the proviso that $R^4$ is selected from fluoro and chloro only when $R^3$ is selected from fluoro and chloro,
or a pharmaceutically acceptable salt thereof, for use in the treatment of an eye disease or eye disorder.

A composition comprising a compound according to formula (IX):

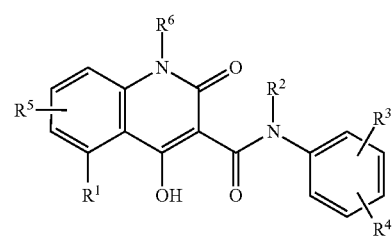

formula (IX)

wherein
$R^1$ is selected from the group consisting of hydrogen, hydroxy, methyl, ethyl, n-propyl, iso-propyl, methoxy, ethoxy, fluoro, chloro, bromo, trifluoromethyl, and trifluoromethoxy,
$R^2$ is selected from the group consisting of hydrogen and C1-C4 alkyl, such as methyl, ethyl, or vinyl,
$R^3$ is selected from the group consisting of hydrogen, hydroxy, methyl, methoxy, fluoro, chloro, bromo, trifluoromethyl, and trifluoromethoxy,
$R^4$ is selected from the group consisting of hydrogen, fluoro and chloro, with the proviso that $R^4$ is selected from fluoro and chloro only when $R^3$ is selected from fluoro and chloro,
$R^5$ is hydrogen or hydroxy, and
$R^6$ is methyl or hydrogen,
or a pharmaceutically acceptable salt thereof, for use in the treatment of an eye disease or eye disorder.

One embodiment of the present disclosure provides for a method for treating an eye disease, said method comprising administering a composition comprising a therapeutically effective amount of a compound according to formula (VI), formula (VII), formula (VIII), for formula (IX), as disclosed herein, or a pharmaceutically acceptable salt thereof.

One embodiment of the present disclosure provides for a use of a compound according to formula (VI), formula (VII), formula (VIII), or formula (IX) as disclosed herein, or a pharmaceutically acceptable salt thereof, for the manufacture of a medicament for the treatment of an eye disease or eye disorder.

Excessive Vascularisation of Eye Tissues

The present disclosure relates to treatment of an eye disease or eye disorder associated with excessive vascularisation of the eye. Such vascularisation may occur in response to external stimuli to the eye, such as excessive stress. Vascularisation may also occur as a natural result of age. Vascularisation of certain eye tissues can be deleterious to eyesight. The eye consists of many different tissues, such as the cornea, the iris, the ciliary body, the choroid, the retina, or the macula. Each of these tissues may be subject to vascularisation.

In one embodiment of the present disclosure, a compound for treatment of a subject is provided, wherein the subject is suffering from vascularisation of the cornea, the iris, the ciliary body, the choroid, the retina, or the macula.

In one embodiment of the present disclosure, a compound for treatment of a subject is provided, wherein the subject is suffering from vascularisation of a tissue in the anterior of the eye, such as the cornea, the iris, or the ciliary body. It is important that the cornea is transparent for functioning eyesight. Vascularisation of the cornea is therefore deleterious to the eyesight of a person. Thus, in a preferred embodiment, the present disclosure provides for a composition comprising a compound of the disclosure for treatment of corneal neovascularisation.

In one embodiment of the present disclosure, the eye disease or eye disorder is selected from the group consisting of corneal neovascularisation, neovascularisation of the iris, neovascularisation of the ciliary body, corneal pannus, choroidal neovascularisation, retinal neovascularisation, wet age-related macular degeneration, proliferative diabetic retinopathy, retinopathy of prematurity, and ischemic retinopathy.

In one embodiment of the disclosure, the eye disease or eye disorder is associated with excessive vascularisation of the eye. In one embodiment of the present disclosure, the eye disease or eye disorder is corneal neovascularisation, neovascularisation of the iris, neovascularisation of the ciliary body, corneal pannus, choroidal neovascularisation, retinal neovascularisation, wet age-related macular degeneration, proliferative diabetic retinopathy, retinopathy of prematurity, or ischemic retinopathy associated with excessive vascularisation of the eye.

Retinopathy is damage to the retina, which may cause vision impairment. Retinopathy can refer to retinal vascular disease or damage to the retina caused by abnormal blood flow. Thus, in one embodiment of the present disclosure, a compound for treatment of a subject is provided, wherein the subject is suffering from proliferative diabetic retinopathy, retinopathy of prematurity, or ischemic retinopathy. Diabetes is a common cause of retinopathy, and diabetic retinopathy is one of the leading causes of blindness in working-aged people. Thus, in an embodiment of the present disclosure, a composition comprising a compound of the disclosure for treatment of a subject is provided, wherein the subject is suffering from proliferative diabetic retinopathy.

In one embodiment of the present disclosure, a compound for treatment of a subject is provided, wherein the subject is suffering from vascularisation of a tissue in the posterior of the eye, such as the choroid, the retina, or the macule. The purpose of the retina is to receive light that the lens has focused, convert the light into neural signals, and send these signals on to the brain for visual recognition. Therefore, any disruption to the retina, such as vascularisation, can affect the eyesight of a person. Thus, in a preferred embodiment of the present disclosure, a composition comprising a compound of the disclosure is provided for treatment of a subject suffering from retinal neovascularisation.

The macula is the central area of the retina. The macula is responsible for the central, high-resolution, colour vision that is possible in good light. Damage to the macula will result in loss of central vision, which can severely affect a person's ability to read and recognise faces. Thus, in the most preferred embodiment of the present disclosure, a composition comprising a compound of the disclosure is provided for treatment of a subject suffering from vascularisation of the macula. Vascularisation of the macula is also known as wet age-related macular degeneration. Thus, in the most preferred embodiment of the present disclosure, a composition comprising a compound of the disclosure is provided for treatment of a subject suffering from wet age-related macular degeneration. In one embodiment of the present disclosure, the wet age-related macular degeneration is associated with excessive vascularisation of the eye.

In a preferred embodiment of the disclosure, the term "an eye disease or eye disorders associated with excessive vascularisation of the eye" does not comprise uveitis or conjunctivitis.

Administration of the Disclosed Compositions Together with VEGF Inhibitors

Vascular endothelial growth factor (VEGF) stimulates formation of blood vessels. VEGF inhibitors have the potential to reduce vascularisation of tissues by binding VEGF. Alternatively, VEGF inhibitors may affect the activity of VEGF by binding to the VEGF receptor.

The compositions of the disclosure may be administered in combination with a VEGF inhibitor for the treatment of an eye disease or eye disorder, such as those associated with excessive vascularisation of the eye. Such combination treatment is potentially more effective at treating the eye disease or eye disorder than the compositions of the disclosure and/or the VEGF inhibitor alone. Thus, in one embodiment of the present disclosure, an eye disease or eye disorder is treated by administration of a composition of the disclosure in combination with administration of a VEGF inhibitor.

VEGF inhibitors comprise antibodies, antibody-derived fragments, recombinant proteins and recombinant fusion proteins such as aflibercept, ranibizumab, bevacizumab, brolucizumab, abicipar pegol, conbercept, and faricimab. Thus, in one embodiment of the present disclosure, an eye disease or eye disorder is treated by administration of a composition of the disclosure in combination with administration of aflibercept, ranibizumab, bevacizumab, brolucizumab, abicipar pegol, conbercept, or faricimab. In a preferred embodiment, an eye disease or eye disorder is treated by administration of a composition of the disclosure in combination with administration of aflibercept, ranibizumab, bevacizumab, or brolucizumab.

The recombinant protein aflibercept (Eylea) has affinity for VEGF-A, VEGF-B, and PGF. This VEGF inhibitor has been shown to be effective in treatment of wet AMD. In one preferred embodiment of the present disclosure, an eye disease or eye disorder is treated by administration of a composition of the disclosure in combination with administration of aflibercept.

The monoclonal antibody fragment ranibizumab has affinity for VEGF-A. This antibody fragment is known to be effective in the treatment of wet AMD. In one embodiment of the present disclosure, an eye disease or eye disorder is treated by administration of a composition of the disclosure in combination with administration of ranibizumab.

Bevacizumab (Avastin) is an IgG1-based antibody which binds VEGF-A. Bevacizumab has been shown to be effective for treatment of wet AMD. Thus, in one embodiment of the present disclosure, an eye disease or eye disorder is treated by administration of a composition of the disclosure in combination with administration of bevacizumab.

Brolucizumab is an sc antibody fragment which has affinity for VEGF-A. In one embodiment of the present disclosure, an eye disease or eye is treated by administration of a composition of the disclosure in combination with administration of bevacizumab.

The peptide abicipar pegol is a known VEGF-A inhibitor. In one embodiment of the present disclosure, an eye disease or eye disorder is treated by administration of a composition of the disclosure in combination with administration of abicipar pegol.

Conbercept is a recombinant fusion protein with affinity for VEGF-A. Thus, in one embodiment of the present disclosure, an eye disease or eye disorder is treated by administration of a composition of the disclosure in combination with administration of conbercept.

The bispecific monoclonal antibody faricimab modulates both angiopoietin-2 and VEGF-A activity. Thus, in one embodiment of the present disclosure, an eye disease or eye disorder is treated by administration of a compound of the disclosure in combination with faricimab.

In one embodiment of the present disclosure, the composition of the disclosure comprises or is administered in combination with an angiogenesis inhibitor. In a specific embodiment of the disclosure, the angiogenesis inhibitor is aflibercept.

In one embodiment of the present disclosure, a composition comprising a compound of the disclosure may be administered to a subject in need thereof via a topical, oral, intravitreal, subconjunctival, retrobulbar, intracameral, or systemic route.

In the treatment of a disease or disorder which is highly localised to one part of the body, such as an eye disease or and eye disorder, it can be advantageous to administer a pharmaceutical directed against that disease or disorder via a route that ensures said pharmaceutical is localised mainly at the site of the disease or disorder. Thus, in a preferred embodiment of the present disclosure, a composition comprising a compound of the disclosure may be administered to a subject in need thereof via a topical, intravitreal, subconjunctival, retrobulbar, or intracameral route.

In one embodiment of the disclosure, the composition of the disclosure is administered in a way to effect systemic administration of the composition. In a further embodiment of the disclosure, the administration of the composition of the disclosure is oral administration.

In the treatment of a disease or disorder, wherein said disease or disorder requires frequent administration of dosages of a pharmaceutical to a subject, it can be advantageous if the pharmaceutical is formulated in a way that allows for self-administration. The person skilled in the art will know which types of formulations are suitable for self-administration.

As outlined herein, the compositions of the invention may be administered in combination with a VEGF inhibitor. Thus, in one embodiment, the composition of the present disclosure and the VEGF inhibitor is comprised within the same formulation and thereby administered simultaneously.

The combination treatment described herein is not limited to compositions comprising both a compound of the disclosure and a VEGF inhibitor. On the contrary, the compound of the invention and the VEGF inhibitor may be administered as different formulations. The choice to administer the compound of the disclosure and the VEGF inhibitor as separate formulations could be motivated by the compound of the disclosure and the VEGF inhibitor having different preferred dosage regimes. For instance, it may be advantageous to administer the compound of the disclosure often, such as daily or weekly, whereas the VEGF inhibitor is better administered infrequently, such as every few months. The choice to administer the compound of the disclosure and the VEGF inhibitor as separate formulations could also be motivated by the compound of the disclosure and VEGF inhibitor not being suitable for the same type of administration route. For instance, the compound of the disclosure might be especially suitable for one type of administration route, such as topical administration, whereas the VEGF inhibitor might be suitable for a second type of administration route, such as intravitreal injection. Thus, in one embodiment, the compound of the disclosure and the VEGF inhibitor are comprised within different formulations, wherein the formulations are administered at different frequencies. In another embodiment, the compound of the disclosure and the VEGF inhibitor are comprised within different formulations, wherein the formulations are administered employing different routes of administration.

VEGF inhibitors are typically administered as intravitreal injections for treatment of eye diseases or eye disorders such as those associated with vascularisation of the eye. Intravitreal injections are often performed at a hospital or at the office of a general practitioner. Intravitreal injections for the treatment of diseases associated with vascularisation of the eye are typically given at a frequency of a few months, such as for instance every month, every 3 months, or every 6 months. Intravitreal injections are given under local anaesthesia. Adverse effects of intravitreal injection include increased pressure in the eye, floaters, inflammation, bleeding, scratched cornea, damage to the retina or surrounding nerves, and infection. Furthermore, the need to visit a general practitioner or a hospital every few months to have the injection performed can be inconvenient, and persons receiving intravitreal injections may find the experience unpleasant and discomforting. Topical treatment with a compound of the disclosure before, during, or in the time period between intravitreal injections with VEGF inhibitors may prolong the period before additional injections of VEGF are needed. Thus, in one embodiment of the present disclosure, topical treatment of an eye disease or eye disorder such as those associated with excessive vascularisation of the eye with a composition comprising the compound of the disclosure effects that intravitreal injections with a VEGF inhibitor are needed less frequently, than had the intravitreal injections of VEGF inhibitor been employed alone. Furthermore, in one embodiment, the compound of the disclosure and the VEGF inhibitor are comprised within different compositions wherein administration of the composition comprising the compound of the disclosure effects treatment of the eye disease or eye disorder and reduces the frequency required of intravitreal VEGF inhibitor injection.

Treatment

In one embodiment of the present disclosure, a composition is provided comprising a compound of the present disclosure. In a further embodiment, a composition is provided comprising a compound of the present disclosure and a pharmaceutically acceptable excipient.

Different routes exist for administration of pharmaceuticals to the eye. For instance, medicaments may be administered topically to the eye. Thus, in one embodiment, a composition comprising a compound of the present disclosure is administered topically to the eye. The person skilled in the art will know which types of administration routes are suitable for administration to the eye.

In one embodiment of the disclosure, a composition comprising a compound of the present disclosure is administered orally.

One embodiment of the present disclosure provides for a composition comprising a compound according to formula (IX):

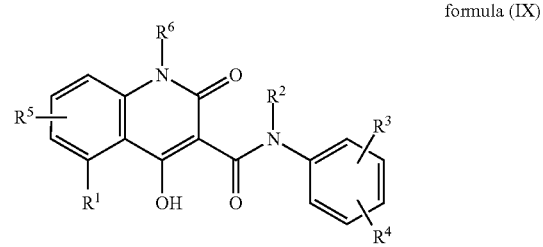

formula (IX)

wherein $R^1$ is selected from the group consisting of hydrogen, hydroxy, methyl, ethyl, n-propyl, iso-propyl, methoxy, ethoxy, fluoro, chloro, bromo, trifluoromethyl, and trifluoromethoxy, R² is selected from the group consisting of hydrogen and C1-C4 alkyl, such as methyl, ethyl, or vinyl, R³ is selected from the group consisting of hydrogen, hydroxy, methyl, methoxy, fluoro, chloro, bromo, trifluoromethyl, and trifluoromethoxy, R⁴ is selected from the group consisting of hydrogen, fluoro and chloro, with the proviso that R⁴ is selected from fluoro and chloro only when R³ is selected from fluoro and chloro, R⁵ is hydrogen or hydroxy, and R⁶ is methyl or hydrogen, or a pharmaceutically acceptable salt thereof, for use in the treatment of an eye disease or eye disorder, wherein the eye disease or eye disorder is wet age-related macular degeneration.

One embodiment of the present disclosure provides for a method of treating wet age-related macular degeneration in a subject, said method comprising administering to a subject a composition comprising a compound of formula (I):

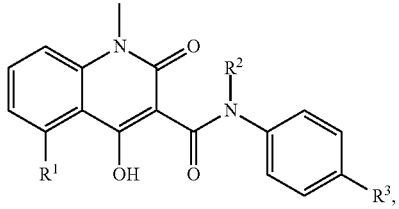

formula (I)

wherein:
R¹ is chloro, R² is ethyl, and R³ is hydrogen,
R¹ is methoxy, R² is methyl, and R³ is trifluoromethyl,
R¹ is chloro, R² is hydrogen, and R³ is hydrogen,
or
R¹ is methoxy, R² is hydrogen, and R³ is trifluoromethyl.

In a further embodiment, the present disclosure provides for a method of treating wet age-related macular degeneration in a subject, said method comprising administering to said subject laquinimod. In another embodiment, the present disclosure provides for a method of treating wet age-related macular degeneration, said method comprising administering to the subject a therapeutically effective amount of tasquinimod. In yet another embodiment, the present disclosure provides for a method of treating wet age-related macular degeneration, said method comprising administering to the subject a therapeutically effective amount of ABR-215691. In yet another embodiment, the present disclosure provides for a method of treating wet age-related macular degeneration, said method comprising administering to the subject a therapeutically effective amount of ABR-215174.

The compounds disclosed herein may be used for the manufacture of medicaments. Thus, in one embodiment of the present invention, a compound of formula (I):

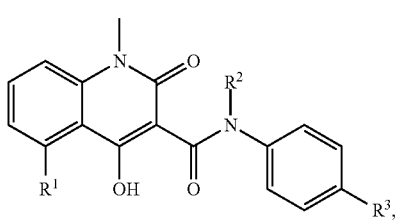

formula (I)

wherein:
R¹ is chloro, R² is ethyl, and R³ is hydrogen,
R¹ is methoxy, R² is methyl, and R³ is trifluoromethyl
R¹ is chloro, R² is hydrogen, and R³ is hydrogen,
or
R¹ is methoxy, R² is hydrogen, and R³ is trifluoromethyl, is used for the manufacture of a medicament for the treatment of wet age-related macular degeneration. In another embodiment, laquinimod is used for the manufacture of a medicament for the treatment of wet age-related macular degeneration. In yet another embodiment, tasquinimod is used for the manufacture of a medicament for the treatment of wet age-related macular degeneration. In yet another embodiment, ABR-215174 is used for the manufacture of a medicament for the treatment of wet age-related macular degeneration. In yet another embodiment, ABR-215691 is used for the manufacture of a medicament for the treatment of wet age-related macular degeneration.

Items

1. A composition comprising:
   a compound according to formula (IX):

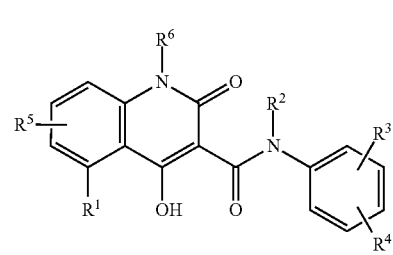

formula (IX)

wherein
R¹ is selected from the group consisting of hydrogen, hydroxy, methyl, ethyl, n-propyl, iso-propyl, methoxy, ethoxy, fluoro, chloro, bromo, trifluoromethyl, and trifluoromethoxy, R² is selected from the group consisting of hydrogen and C1-C4 alkyl, such as methyl, ethyl, or vinyl, R³ is selected from the group consisting of hydrogen, hydroxy, methyl, methoxy, fluoro, chloro, bromo, trifluoromethyl, and trifluoromethoxy, R⁴ is selected from the group consisting of hydrogen, fluoro and chloro, with the proviso that R⁴ is selected from fluoro and chloro only when R³ is selected from fluoro and chloro, R⁵ is hydrogen or hydroxy, and R⁶ is methyl or hydrogen, or a pharmaceutically acceptable salt thereof, for use in the treatment of an eye disease or eye disorder.

2. The composition for use according to item 1, wherein the compound is a compound according to formula (VIII):

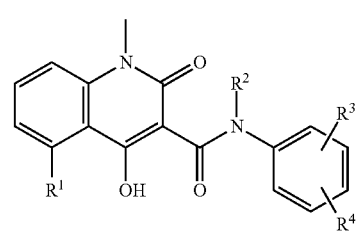

formula (VIII)

wherein
R¹ is selected from the group consisting of hydrogen, hydroxy, methyl, ethyl, n-propyl, iso-propyl, methoxy, ethoxy, fluoro, chloro, bromo, trifluoromethyl, and trifluoromethoxy,
R² is selected from the group consisting of hydrogen and C1-C4 alkyl, such as methyl, ethyl or vinyl,
R³ is selected from the group consisting of hydrogen, hydroxy, methyl, methoxy, fluoro, chloro, bromo, trifluoromethyl, and trifluoromethoxy, and
R⁴ is selected from the group consisting of hydrogen, fluoro and chloro, with the proviso that R⁴ is selected from fluoro and chloro only when R³ is selected from fluoro and chloro,
or a pharmaceutically acceptable salt thereof.

3. The composition for use according to any one of the preceding items, wherein the compound is a compound according to formula (VII):

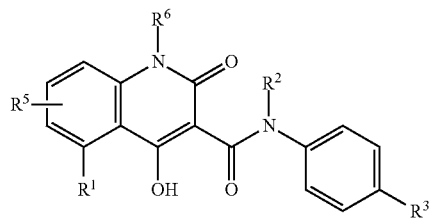

formula (VII)

wherein:
R¹ is methoxy or hydroxy,
R² is methyl or hydrogen,
R³ is trifluoromethyl,
R⁵ is hydrogen or hydroxy, and
R⁶ is methyl or hydrogen,
or a pharmaceutically acceptable salt thereof.

4. The composition for use according to any one of the preceding items, wherein the compound is a compound according to formula (VI):

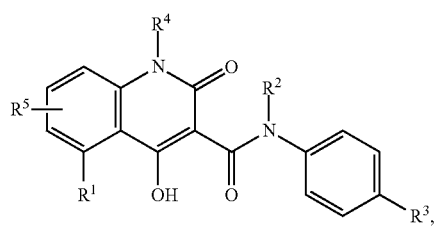

formula (VI)

wherein
R¹ is chloro,
R² is ethyl or hydrogen,
R³ is hydrogen or hydroxy,
R⁵ is hydrogen or hydroxy, and
R⁶ is methyl or hydrogen,
or a pharmaceutically acceptable salt thereof.

5. A composition comprising 5'-chloro-1-ethyl-1'-methyl-2'H-spiro[indoline-3,3'-quinoline]-2,2',4'(1'H)-trione, or a pharmaceutically acceptable salt thereof, for use in the treatment of an eye disease or eye disorder.

6. The composition for use according to any one of the preceding items, wherein the compound is a compound selected from the group consisting of:
laquinimod,
5-chloro-N-ethyl-4-hydroxy-N-(4-hydroxyphenyl)-1-methyl-2-oxo-1,2-dihydroquinoline-3-carboxamide,
5-chloro-4-hydroxy-1-methyl-2-oxo-N-phenyl-1,2-dihydroquinoline-3-carboxamide,
5-chloro-N-ethyl-4-hydroxy-2-oxo-N-phenyl-1,2-dihydroquinoline-3-carboxamide,
5-chloro-N-ethyl-4,8-dihydroxy-1-methyl-2-oxo-N-phenyl-1,2-dihydroquinoline-3-carboxamide,
5-chloro-N-ethyl-4,7-dihydroxy-1-methyl-2-oxo-N-phenyl-1,2-dihydroquinoline-3-carboxamide,
5-chloro-N-ethyl-4,6-dihydroxy-1-methyl-2-oxo-N-phenyl-1,2-dihydroquinoline-3-carboxamide,
5-chloro-4-hydroxy-1-methyl-2-oxo-N-phenyl-N-vinyl-1,2-dihydroquinoline-3-carboxamide,
5-chloro-N-ethyl-4-hydroxy-N-(4-hydroxyphenyl)-1-methyl-2-oxo-1,2-dihydroquinoline-3-carboxamide,
N-ethyl-4-hydroxy-1-methyl-2-oxo-N-phenyl-1,2-dihydroquinoline-3-carboxamide,
tasquinimod,
4-hydroxy-5-methoxy-N-methyl-2-oxo-N-(4-(trifluoromethyl)phenyl)-1,2-dihydroquinoline-3-carboxamide,
4,5-dihydroxy-N,1-dimethyl-2-oxo-N-(4-(trifluoromethyl)phenyl)-1,2-dihydroquinoline-3-carboxamide,
4-hydroxy-5-methoxy-1-methyl-2-oxo-N-(4-(trifluoromethyl)phenyl)-1,2-dihydroquinoline-3-carboxamide,
4,6-dihydroxy-5-methoxy-N,1-dimethyl-2-oxo-N-(4-(trifluoromethyl)phenyl)-1,2-dihydroquinoline-3-carboxamide,
4,7-dihydroxy-5-methoxy-N,1-dimethyl-2-oxo-N-(4-(trifluoromethyl)phenyl)-1,2-dihydroquinoline-3-carboxamide, and
4,8-dihydroxy-5-methoxy-N,1-dimethyl-2-oxo-N-(4-(trifluoromethyl)phenyl)-1,2-dihydroquinoline-3-carboxamide,
or a pharmaceutically acceptable salt thereof.

7. The composition for use according to any one of the preceding items, wherein the compound is a compound of formula (I):

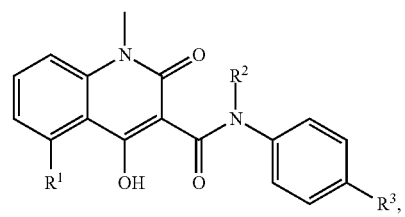

formula (I)

wherein:
R¹ is chloro, R² is ethyl or hydrogen, and R³ is hydrogen,
or
R¹ is methoxy, R² is methyl or hydrogen, and R³ is trifluoromethyl;
or a pharmaceutically acceptable salt thereof.

8. The composition for use according to any one of the preceding items, wherein the compound is laquinimod or a pharmaceutically acceptable salt thereof.

9. The composition for use according to any one of the preceding items, wherein the compound is tasquinimod, or a pharmaceutically acceptable salt thereof.

10. The composition for use according to any one of the preceding items, wherein the compound is a compound of formula (IV):

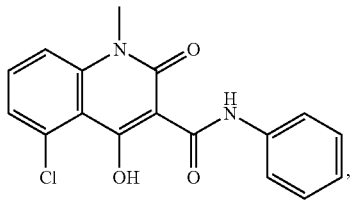

formula (IV)

or a pharmaceutically acceptable salt thereof.

11. The composition for use according to any one of the preceding items, wherein the compound is a compound of formula (V):

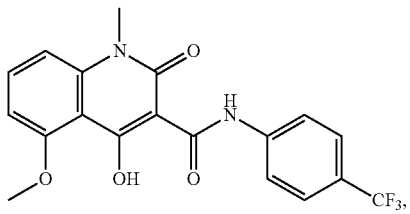

formula (V)

or a pharmaceutically acceptable salt thereof.

12. The composition for use according to any one of the preceding items, wherein the eye disease or eye disorder is selected from the group consisting of corneal neovascularisation, neovascularisation of the iris, neovascularisation of the ciliary body, corneal pannus, choroidal neovascularisation, retinal neovascularisation, wet age-related macular degeneration, proliferative diabetic retinopathy, retinopathy of prematurity, and ischemic retinopathy.

13. The composition for use according to any one of the preceding items, wherein the eye disease or eye disorder is selected from the group consisting of corneal neovascularisation, neovascularisation of the iris, neovascularisation of the ciliary body, and corneal pannus.

14. The composition for use according to any one of the preceding items, wherein the eye disease or eye disorder is corneal neovascularisation.

15. The composition for use according to any one of the preceding items, wherein the eye disease or eye disorder is selected from the group consisting of proliferative diabetic retinopathy, retinopathy of prematurity, and ischemic retinopathy.

16. The composition for use according to any one of the preceding items, wherein the eye disease or eye disorder is proliferative diabetic retinopathy.

17. The composition for use according to any one of the preceding items, wherein the eye disease or eye disorder is retinopathy of prematurity.

18. The composition for use according to any one of the preceding items, wherein the eye disease or eye disorder is ischemic retinopathy.

19. The composition for use according to any one of the preceding items, wherein the eye disease or eye disorder is selected from the group consisting of choroidal neovascularisation, retinal neovascularisation, and wet age-related macular degeneration.

20. The composition for use according to any one of the preceding items, wherein the eye disease or eye disorder is choroidal neovascularisation.

21. The composition for use according to any one of the preceding items, wherein the eye disease or eye disorder is retinal neovascularisation.

The composition for use according to any one of the preceding items, wherein the eye disease or eye disorder is wet age-related macular degeneration.

22. The composition for use according to any one of the preceding items, wherein the eye disease or eye disorder is not uveitis or conjunctivitis.

23. The composition for use according to any one of the preceding items, wherein the eye disease or eye disorder is associated with excessive vascularisation of the eye.

24. The composition for use according to any one of the preceding items, wherein the composition comprises or is administered in combination with an angiogenesis inhibitor, such as aflibercept.

25. The composition for use according to any one of the preceding items, wherein the composition is administered in combination with one or more VEGF inhibitors.

26. The composition for use according to any one of the preceding items, wherein the composition is administered in combination with one VEGF inhibitor.

27. The composition for use according to any one of the preceding items, wherein the composition further comprises one or more VEGF inhibitors.

28. The composition for use according to any one of the preceding items, wherein the composition further comprises one VEGF inhibitor.

29. The composition for use according to any one of the preceding items, wherein the VEGF inhibitor is selected from the group consisting of aflibercept, ranibizumab, bevacizumab, brolucizumab, abicipar pegol, conbercept, and faricimab.

30. The composition for use according to any one of the preceding items, wherein the VEGF inhibitor is selected from the group consisting of aflibercept, ranibizumab, bevacizumab, and brolucizumab.

31. The composition for use according to any one of the preceding items, wherein the VEGF inhibitor is aflibercept.

32. The composition for use according to any one of the preceding items, wherein the VEGF inhibitor is ranibizumab.

33. The composition for use according to any one of the preceding items, wherein the VEGF inhibitor is bevacizumab.

34. The composition for use according to any one of the preceding items, wherein the VEGF inhibitor is brolucizumab.

35. The composition for use according to any one of the preceding items, wherein the VEGF inhibitor is abicipar pegol.

36. The composition for use according to any one of the preceding items, wherein the VEGF inhibitor is conbercept.

37. The composition for use according to any one of the preceding items, wherein the VEGF inhibitor is faricimab.

38. The composition for use according to any one of the preceding items, wherein the composition comprises or is administered in combination with at least one pharmaceutically acceptable excipient.

39. The composition for use according to any one of the preceding items, wherein the route of administration is topical, oral, intravitreal, subconjunctival, retrobulbar, intracameral, or systemic.

40. The composition for use according to any one of the preceding items, wherein the route of administration is topical.

41. The composition for use according to any one of the preceding items, wherein the route of administration is oral.

42. The composition for use according to any one of the preceding items, wherein the route of administration is intravitreal.

43. The composition for use according to any one of the preceding items, wherein the route of administration is subconjunctival.

44. The composition for use according to any one of the preceding items, wherein the route of administration is retrobulbar.

45. The composition for use according to any one of the preceding items, wherein the route of administration is intracameral.

46. The composition for use according to any one of the preceding items, wherein the route of administration is systemic.

47. A method of treating wet age-related macular degeneration, said method comprising administering a composition comprising a therapeutically effective amount of a compound according to formula (IX):

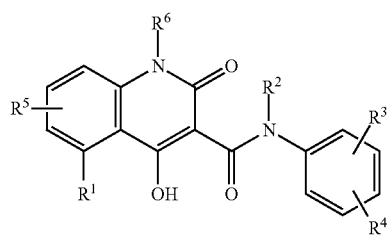

formula (IX)

wherein
$R^1$ is selected from the group consisting of hydrogen, hydroxy, methyl, ethyl, n-propyl, iso-propyl, methoxy, ethoxy, fluoro, chloro, bromo, trifluoromethyl, and trifluoromethoxy, $R^2$ is selected from the group consisting of hydrogen and C1-C4 alkyl, such as methyl, ethyl, or vinyl, $R^3$ is selected from the group consisting of hydrogen, hydroxy, methyl, methoxy, fluoro, chloro, bromo, trifluoromethyl, and trifluoromethoxy, $R^4$ is selected from the group consisting of hydrogen, fluoro and chloro, with the proviso that $R^4$ is selected from fluoro and chloro only when $R^3$ is selected from fluoro and chloro, $R^5$ is hydrogen or hydroxy, and $R^6$ is methyl or hydrogen, or a pharmaceutically acceptable salt thereof to a subject in need thereof.

48. Use of a compound according to formula (IX):

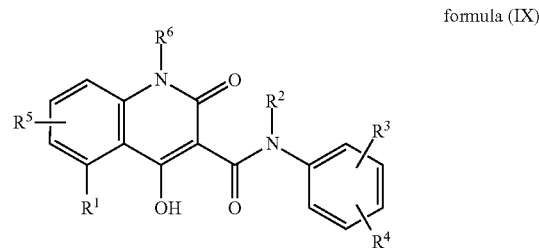

formula (IX)

wherein
$R^1$ is selected from the group consisting of hydrogen, hydroxy, methyl, ethyl, n-propyl, iso-propyl, methoxy, ethoxy, fluoro, chloro, bromo, trifluoromethyl, and trifluoromethoxy, $R^2$ is selected from the group consisting of hydrogen and C1-C4 alkyl, such as methyl, ethyl, or vinyl, $R^3$ is selected from the group consisting of hydrogen, hydroxy, methyl, methoxy, fluoro, chloro, bromo, trifluoromethyl, and trifluoromethoxy, $R^4$ is selected from the group consisting of hydrogen, fluoro and chloro, with the proviso that $R^4$ is selected from fluoro and chloro only when $R^3$ is selected from fluoro and chloro, $R^5$ is hydrogen or hydroxy, and $R^6$ is methyl or hydrogen, or a pharmaceutically acceptable salt thereof for the manufacture of a medicament for the treatment of an eye disease or eye disorder.

Example 1: Suppression of Choroidal Neovascularisation in a Laser-Induced Choroidal Neovascularisation Rat Model Study Design Forty-eight (48) Brown Norway pigmented rats were divided into six (6) groups of eight (8) animals. Choroidal neovascularization was induced using a 532 nm argon laser photocoagulator (six (6) 75 µm-sized spots at 150 mW for 0.1 sec duration) in the right eyes on Day 0. The test item was administered three times a day by instillation or twice a day by oral administration from Day 0 (DO) just after ChNV induction to Day 21 (last day of the study). Control item (vehicle) was instilled three times a day and the reference item (Dexamethasone in olive oil) was administered by daily oral administration from the Day 0 just after induction of neovascularization to Day 21. Fundus neovessels were evaluated in the right eyes on Days 14 and 21 using Heidelberg's Retinal Angiograph (HRA). Lesion size was determined on choroid flatmounts labelled with Isolectin-B4 at the end of the in vivo period.

Induction of Neovascularisation

On Day 0, animals were anesthetized by an intramuscular injection of a mix of xylazine (5 mg/kg) and ketamine (25 mg/kg). Pupils from the right eyes were dilated by instillation of one drop of 0.5% tropicamide. Then, six (6) choroidal burns (75 µm spot size) were done through a slit-lamp, with a contact lens, around the optic disc, between the main vessel branches using an argon laser photocoagulator (532 nm; 150 mW; 0.1 sec duration). Production of a bubble at the time of laser treatment confirmed the rupture of Bruch's membrane.

Route and Method of Administration

Test, control, or reference items were administered topically by instillation (10 μL each) or by oral route (1 mL/kg) from Day 0 (just after the induction) to Day 21 (end of the study). Test and control items were administered three times a day (for instillation) and two times a day (for oral administration). Reference item was administered once a day by oral route.

Body Weights

The body weight of all animals was recorded before the start of the study, then once every week.

Fluorescein Angiography

Fluorescein angiography was performed on Days 14 and 21 using an HRA (Heidelberg's Retinal Angiograph). After anaesthesia (same mix used for ChNV induction) and pupillary dilation, 250 μL/100 g (body weight) of a 10% sodium fluorescein was injected subcutaneously using a 26-G insulin syringe, and fluorescein photos were recorded 10 minutes after dye injection.

Evaluation by Fluorescein Angiography

The leakage of fluorescein on the angiograms were evaluated by two examiners in a masked fashion and graded as follows:

Score 0, no leakage;

Score 1, slightly stained;

Score 2, moderately stained;

Score 3, strongly stained.

When the two scores assigned to a particular lesion do not coincide, the higher score was used for analysis.

Data Processing

Statistical analysis, using Mann-Whitney U test or appropriate statistical model, were performed on the scoring of lesions visualized by HRA from each animal and on the scoring of the flat mounted preparations.

Animal Behaviour and Mortality

The general behaviour and appearance of all animals were observed and noted in the raw data. No particular sign was observed and the general behaviour and appearance of animals were normal. All animals survived until the scheduled euthanasia.

Animal Body Weight

Animal body weights were recorded before induction and treatment (baseline) and then once a week. Animal body weights were within the normal range at the baseline: 166-202 g (min–max, n=48). On Day 21, no significant difference between test and control items was observed. Animals treated with the reference item (dexamethasone) showed a 21% body weight loss during the study. This loss is an expected adverse effect of orally dosed corticosteroid.

Angiography Evaluations

The grading of fluorescein angiographies (FA) was based on the fluorescence intensity for each lesion. For each treatment group, results were expressed as the group mean score per time-point. Table 1 summarises the evaluation of FA recorded at 10 min on Days 14 and 21 (n=8 animals per group, right eyes). A statistical analysis was performed on the median of the individual intensity scores, using a Kruskall-Wallis test followed by a Mann & Whitney U multiple comparison test, which was used to compare each test, control or reference group.

TABLE 1 evaluation of FA per treatment group.

| Treatment | Route of Administration | Dosing-regimen | Time-point | Mean score of fluorescein leakage Mean (n = nb evaluated spots/48) | % of reduction vs respective vehicle |
|---|---|---|---|---|---|
| Laquinimod | Instillations | 5% 3×/day | Day 14 | 0.7 (n = 38) | 0% |
| | | | Day 21 | 0.4 (n = 45) | 63% |
| | | 1% 3×/day | Day 14 | 1.1 (n = 36) | <0% |
| | | | Day 21 | 1.2 (n = 46) | <0% |
| | | 0.2% 3×/day | Day 14 | 0.7 | 0% |
| | | | Day 21 | 0.9 (n = 42) | 18% |
| | Per os | 1 mg/kg | Day 14 | 0.8 (n = 42) | <0% |
| | | 2×/day | Day 21 | 0.9 (n = 38) | 18% |
| Laquinimod vehicle | Instillations | — | Day 14 | 0.7 (n = 35) | — |
| | | 3×/day | Day 21 | 1.1 (n = 38) | — |
| Dexamethasone | Per os | 0.5 mg/kg | Day 14 | 0.7 (n = 48) | 71% |
| | | 1×/day | Day 21 | 0.8 (n = 48) | 73% |

(per os = oral)

Conclusion

On Day 14 and Day 21, 63% and 66% of the evaluated spots were leaking in vehicle-treated animals, respectively, indicating the formation and the persistence of ChNV. However, daily topical administration of laquinimod effectively reduces vascular leakage, indicating that laquinimod is effectively counteracting the ChNV.

Example 2: Suppression of VEGF and bFGF Induced Neovascularisation

Method for Assessment of Area of Neovascularisation

The area of the neovascularisation can be measured using the formula:

$$Area = 0.2 \cdot VL \cdot CH \cdot \pi$$

wherein vessel length (VL) and continuous circumferential zone (in clock hours=CH) are measured as defined in FIG. 1.

Treatment with Laquinimod of VEGF Induced Corneal Vascularisation

Hydron pellets for induction of vascularisation were prepared from stimulant (VEGF) and binding agent (sucralfate).

53 CR female C57BL/6 mice aged 6 to 8 weeks were prepared for surgery by anesthetising with 90 mg/kg of pentobarbital, ip. Corneal vascularisation was induced by placement of a pellet in a corneal pocket cut in one eye. Signs for ocular irritation or infection were carefully monitored.

Figure 2:
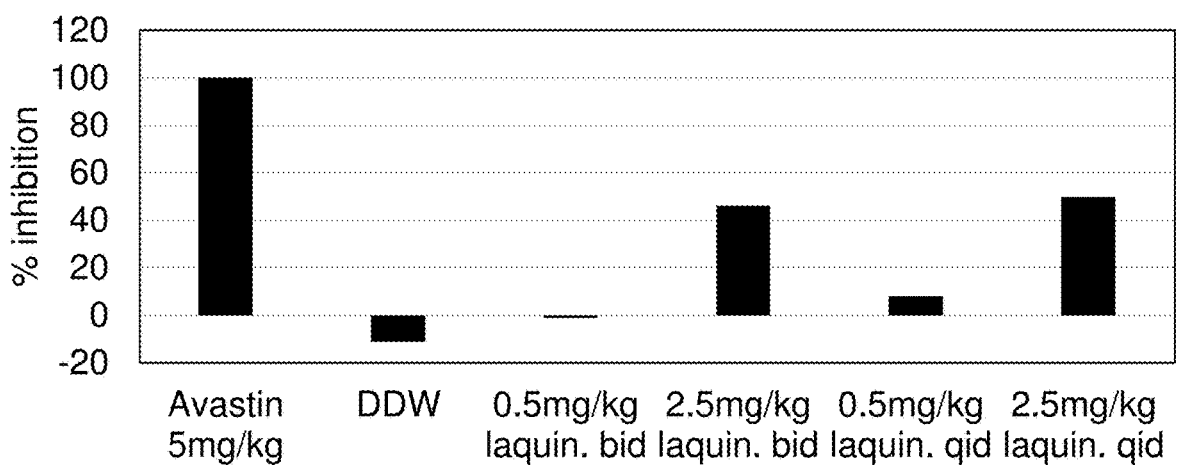
FIG. 2: Inhibition of corneal vascularisation induced by VEGF. Laquin.=laquinimod. Avastin 5 mg/kg provides for 100% inhibition (reference). Dosage of 0.5 mg/kg laquinimod bid. provides for no inhibition. Dosage of 2.5 mg/kg laquinimod bid. provides for 46% inhibition. Dosage of 0.5 mg/kg laquinimod qid. provides for 8% inhibition. Dosage of 2.5 mg/kg laquinimod qid. provides for 50% inhibition.

Dosages of laquinimod in DI (deionised) water, vehicle (DDW=double distilled water), and avastin (positive control) were applied directly to the eye containing the pellet. Vascularisation was measured on day 8. Treatment regimen is shown in Table 2. Results are shown in Table 3 and FIG. 2.

TABLE 2

Treatment regimes for induction of corneal vascularisation with VEGF and subsequent administration of laquinimod.

| | | Treatment regimen 1 | | | | Treatment regimen 2 | | | |
|---|---|---|---|---|---|---|---|---|---|
| Group | n | Agent | ng/animal | Route | Schedule | Agent | µg/animal | Route | Schedule |
| 1 | 8 | VEGF | 129 | cp | qd · 1 | — | — | — | — |
| 2 | 4 | VEGF | 129 | cp | qd · 1 | avas. | 5* | ip | qd × 7 |
| 3 | 4 | VEGF | 129 | cp | qd · 1 | veh. | — | topical | qd × 7 first day 2 doses |
| 4 | 8 | VEGF | 129 | cp | qd · 1 | laqui. | 10 | topical | bid × 7 first day 1 dose |
| 5 | 8 | VEGF | 129 | cp | qd · 1 | laqui. | 50 | topical | bid × 7 first day 1 dose |
| 6 | 8 | VEGF | 129 | cp | qd · 1 | laqui. | 10 | topical | qid × 7 first day 2 doses |
| 7 | 8 | VEGF | 129 | cp | qd · 1 | laqui. | 50 | topical | qid × 7 first day 2 doses |

*mg/kg
laqui. = laquinimod
veh. = vehicle
avas. = avastin

TABLE 3 results for treatment of corneal vascularisation induced by VEGF.

| Group | n | Pellet agent | Area of vasc. | Area percent of positive control |
|---|---|---|---|---|
| 1 | 8 | VEGF | 1.47 ± 0.09 | — |
| 2 | 4 | VEGF | 0.00 ± 0.00 | 0% |
| 3 | 4 | VEGF | 1.63 ± 0.13 | 111% |
| 4 | 8 | VEGF | 1.49 ± 0.13 | 101% |
| 5 | 7 | VEGF | 0.79 ± 0.06 | 54% |
| 6 | 8 | VEGF | 1.35 ± 0.09 | 92% |
| 7 | 8 | VEGF | 0.74 ± 0.11 | 50% | vasc. = vascularisation.

Treatment of vascularisation induced by VEGF showed dosage-dependent effect upon administration of laquinimod: low dosage (0.5 mg/kg, bid, group 4) did not provide for any inhibition. Increasing the frequency administration only provided for little inhibition (0.5 mg/kg, qid, group 6, 8% inhibition). Increasing dosage provided for good inhibition of vascularisation, both at few (2.5 mg/kg, bid, group 5, 46% inhibition) and many (2.5 mg/kg, qid, group 7, 50% inhibition) dosages per day.

Treatment with Laquinimod of bFGF Induced Corneal Vascularisation

Hydron pellets for induction of vascularisation were prepared from stimulant (bFGF) and binding agent (sucralfate).

47 CR female C57BL/6 mice aged 6 to 8 weeks were prepared for surgery by anesthetising with 90 mg/kg of pentobarbital, ip. Corneal vascularisation was induced by placement of a pellet in a corneal pocket cut in one eye. Signs for ocular irritation or infection were carefully monitored.

Figure 3:
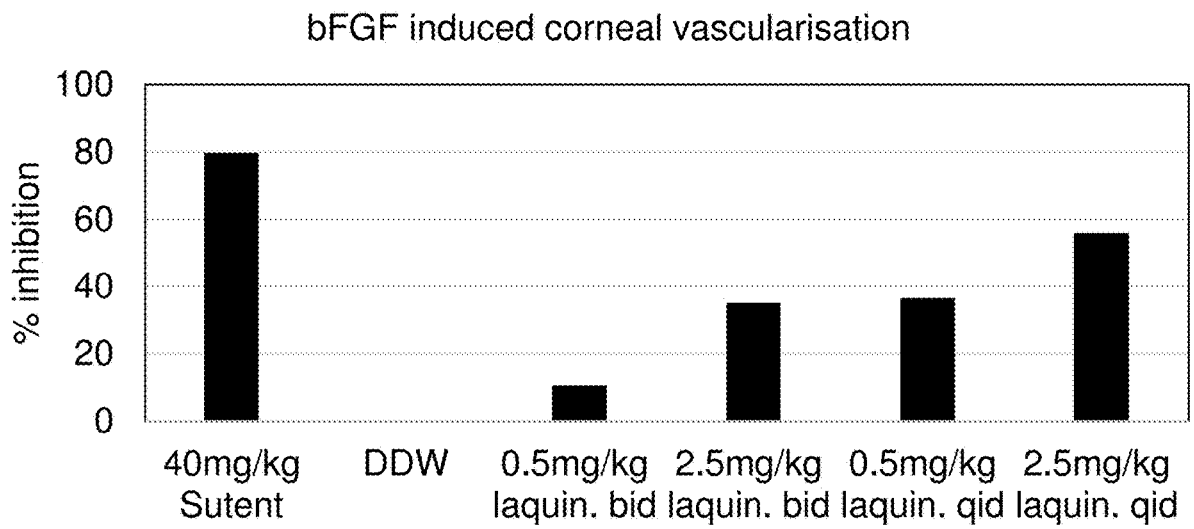
FIG. 3: Inhibition of corneal vascularisation induced by bFGF. Laquin.=laquinimod. Sutent 40 mg/kg provides for 80% inhibition. Dosage of 0.5 mg/kg laquinimod big. provides for 11% inhibition. Dosage of 2.5 mg/kg laquinimod bid. provides for 35% inhibition. Dosage of 0.5 mg/kg laquinimod qid. provides for 37% inhibition. Dosage of 2.5 mg/kg laquinimod qid. provides for 56% inhibition.

Dosages of laquinimod in DI (deionised) water, vehicle (DDW=double distilled water), and avastin (positive control) were applied directly to the eye containing the pellet. Vascularisation was measured on day 6. Treatment regimen is shown in Table 4. Results are shown in Table 5 and FIG. 3.

TABLE 4

Treatment regimes for induction of corneal vascularisation with bFGF and subsequent administration of laquinimod.

| | | Treatment regimen 1 | | | | Treatment regimen 2 | | | |
|---|---|---|---|---|---|---|---|---|---|
| Group | n | Agent | ng/animal | Route | Schedule | Agent | µg/animal | Route | Schedule |
| 1 | 8 | bFGF | 200 | cp | qd · 1 | — | — | — | — |
| 2 | 6 | bFGF | 200 | cp | qd · 1 | sutent | 5* | po | qd × 5 |
| 3 | 4 | bFGF | 200 | cp | qd · 1 | veh. | — | topical | qd × 5 first day 2 doses |
| 4 | 6 | bFGF | 200 | cp | qd · 1 | laqui. | 10 | topical | bid × 5 first day 1 dose |
| 5 | 6 | bFGF | 200 | cp | qd · 1 | laqui. | 50 | topical | bid × 5 first day 1 dose |

TABLE 4-continued

Treatment regimes for induction of corneal vascularisation with bFGF and subsequent administration of laquinimod.

| | | Treatment regimen 1 | | | | Treatment regimen 2 | | | |
|---|---|---|---|---|---|---|---|---|---|
| Group | n | Agent | ng/animal | Route | Schedule | Agent | μg/animal | Route | Schedule |
| 6 | 6 | bFGF | 200 | cp | qd · 1 | laqui. | 10 | topical | qid × 5 first day 2 doses |
| 7 | 6 | bFGF | 200 | cp | qd · 1 | laqui. | 50 | topical | qid × 5 first day 2 doses |

*mg/kg
laqui. = laquinimod
veh. = vehicle

TABLE 5 results for treatment corneal vascularisation induced by bFGF

| Group | n | Pellet Agent | Area of vasc. | Area percent of positive control |
|---|---|---|---|---|
| 1 | 8 | bFGF | 3.54 ± 0.10 | — |
| 2 | 6 | bFGF | 0.72 ± 0.08 | 20% |
| 3 | 4 | bFGF | 3.54 ± 0.15 | 100% |
| 4 | 6 | bFGF | 3.16 ± 0.06 | 89% |
| 5 | 6 | bFGF | 2.30 ± 0.23 | 65% |
| 6 | 6 | bFGF | 2.25 ± 0.16 | 63% |
| 7 | 6 | bFGF | 1.56 ± 0.15 | 44% | vasc. = vascularisation.

Conclusion

Treatment of vascularisation induced by bFGF showed dosage-dependent effect upon administration of laquinimod: low dosage (0.5 mg/kg, bid, group 4) inhibited 11% of the vascularisation whereas higher dosage (2.5 mg/kg, bid, group 5) inhibited 35% of the vascularisation. Increasing the frequency of dosage improved inhibition further, with many low dosages (0.5 mg/kg, qid, group 6) providing for a similar inhibition (37%) as few large doses (group 5). Many daily, large dosages (2.5 mg/kg, qid, group 7) provided for even further inhibition (56%) of vascularisation.

Example 3: Laquinimod and ABR-215174 have an Effect on LPS-Activated Microglia-Induced Human Retinal Microvascular Endothelial Cells Tube Formation Methods The following experimental groups were included in the study:

| | |
|---|---|
| Group 1: | Control (Vehicle, 0.1% DMSO) |
| Group 2: | Sulforaphane (10 μM, positive control, anti-angiogenic effects) |
| Group 3: | Aflibercept ("Eylea" 40 μg/ml, positive control, partial anti-angiogenic effects) |
| Group 4: | ABR-215174 (0.1 μM) |
| Group 5: | ABR-215062 (10 μM) |

Human retinal microvascular endothelial cells (HRMECs) were purchased from Neuromics (Cat #HEC09, Lot #2872) and cultured according to manufacturer's instructions in Endo-Growth media (Cat #EKG001, Lot #EKG0011902269) supplemented with Endothelial Growth Factor (Cat #EKG001, Lot #EGK00125) on AlphaBiocoat coated T25 flasks at 37° C. 5% $CO_2$.

Primary human microglia from brain were purchased from Celprogen (Cat #37089-01, Lot #1614454-01) and cultured in microglia complete growth media with antibiotics (Cat #M37089-01, Lot #2010089205-03) supplemented with 10% standard fetal bovine serum (Neuromics, Lot #042P20) on poly-L-Lysine (PLL, 50 mg/ml) coated T25 flasks at 37° C. 5% $CO_2$.

Human microglia were seeded onto PLL coated cell culture inserts (Sarstedt, Cat #83.3932.040) at 103000 cells/$cm^2$. Microglia were treated with study compounds, aflibercept and vehicle for 24 hours prior to lipopolysaccharide (LPS) activation using following concentrations in microglia complete growth media:

Vehicle (0.1% DMSO)
Aflibercept (Eylea®, 40 g/ml), 0.1% DMSO
ABR-215174 (0.1 μM), 0.1% DMSO
ABR-215062 (10 μM), 0.1% DMSO The method for co-cultures of microglia and HRMECs was modified from protocol described by Ding et al. 2018 (Ding X, Gu R, Zhang M, Ren H, Shu Q, Xu G, Wu H. Microglia enhanced the angiogenesis, migration and proliferation of co-cultured RMECs. BMC Ophthalmol. 2018, 18(1):249. doi: 10.1186/s12886-018-0886-z. PMID: 30223824; PMCID: PMC6142340) and Ji Cho et al. 2019 (Ji Cho M, Yoon S J, Kim W, Park J, Lee J, Park J G, Cho Y L, Hun Kim J, Jang H, Park Y J, Lee S H, Min J K. Oxidative stress-mediated TXNIP loss causes RPE dysfunction. Exp Mol Med. 2019 Oct. 15; 51(10):1-13. doi: 10.1038/s12276-019-0327-y. PMID: 31615975; PMCID: PMC6802648). Microglia was activated with LPS (100 ng/ml) in microglia complete growth media without FBS with simultaneous treatment of freshly prepared study compounds, Eylea and vehicle for 24 hours. HRMECs were incubated in basal Endo-Growth media for 24 hours before co-culturing.

HRMECs were seeded onto Matrigel® coated 24-well plate (42000 cells/$cm^2$) and simultaneously treated of freshly prepared study compounds, aflibercept and sulforaphane in basal Endo-Growth media:

Vehicle (0.1% DMSO)
Sulforaphane (10 M), 0.1% DMSO
Aflibercept (Eylea®, 40 μg/ml), 0.1% DMSO
ABR-215174 (0.1 μM), 0.1% DMSO
ABR-215062 (10 μM), 0.1% DMSO Media in microglia inserts containing LPS was replaced to corresponding freshly prepared study compounds, aflibercept and sulforaphane in basal Endo-Growth media. Inserts containing activated microglia were transferred into the 24-wells containing HRMECs. The co-cultures were incubated at +37° C. 5% $CO_2$, stained with calcein-AM (5 μM)

for 30 min and imaged using a fluorescence microscope (Leica Thunder 3D Tissue Imager, Leica Microsystems).

Images were analyzed using the AngioTool software (Zudaire E, Gambardella L, Kurcz C, Vermeren S (2011) A Computational Tool for Quantitative Analysis of Vascular Networks. PLOS ONE 6(11): e27385. https://doi.org/10.1371/journal.pone.0027385) for ImageJ (NIH public domain). Total tube area, tube length, density, lacunarity, and branching index (number of junctions and endpoints) were quantified.

Images were analyzed using AngioTool software (NIH, Bethesda, Md.; available in the public domain) for the following readouts: average vessels length, total vessels length, vessel area, vessels percentage area, total number of junctions, density of junctions, total number of endpoints, and mean lacunarity. Raw data were plotted in mm or μm (and mm2 or ρm2) for length and area measurements. Raw data for each of the readouts was plotted and analyzed by ordinary one-way ANOVA with Dunnett's multiple comparisons post-hoc test.

Effect size was calculated by subtracting the mean of the vehicle group from each value, then normalizing the data to the sulforaphane (positive control) condition, such that the average for sulforaphane group is equal to a maximal effect size (100%), and for vehicle is equal to no effect size (0%). Effect size data were analyzed by non-parametric Kruskal-Wallis test, with Dunn's multiple comparisons post-hoc test.

Results and Conclusion

Figure 4:
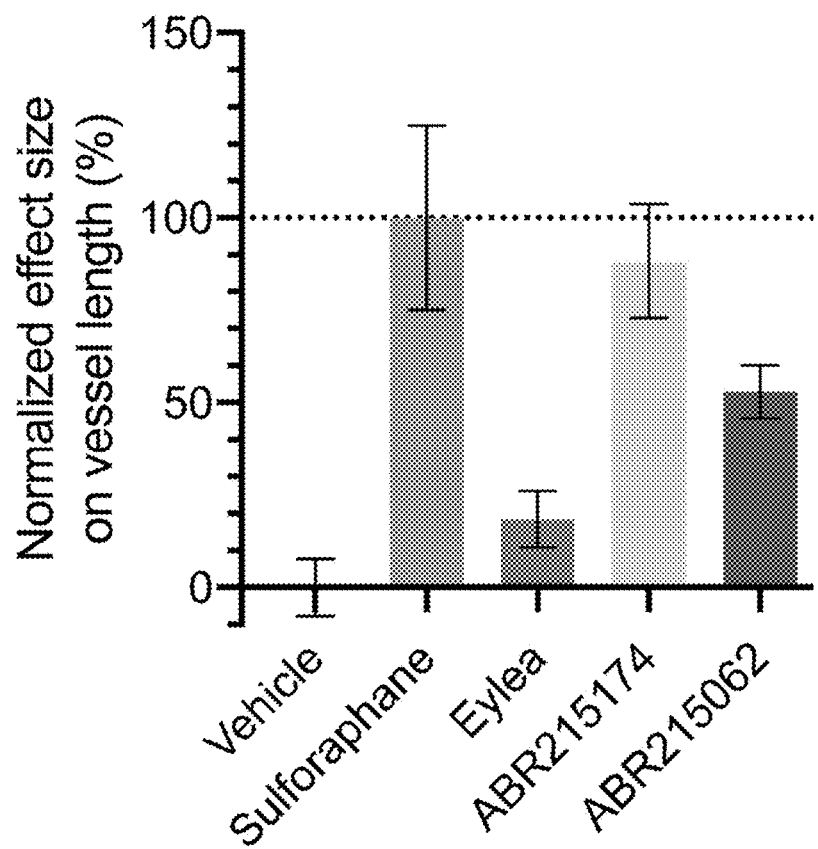
FIG. 4: Normalized effect size on average vessel length. Data was normalised such that vehicle has 0% average effect size, and the positive control sulforaphane has 100% average effect size. Eylea trended towards an increased effect size (18% effect size). Test compound ABR215174 (88.2% effect size) is significantly increased in effect size compared to vehicle. Test compound ABR215062 trended towards increased effect size (53% effect size).

The difference between normalized effect size on average vessel length between sulforaphane and vehicle groups reached statistical significance (FIG. 4). Test compound ABR215174 (88.2% effect size) was significantly increased in effect size on average vessel length compared to vehicle. Effect size of Eylea (18% effect size) and test compound ABR215062 (53% effect size), although not statistically significant, trended towards an increased effect size on average vessel length.

Since sulphoraphane is a known and well-accepted positive control for prevention of angiogenesis, these results indicate that the test compounds ABR215174 and ABR215062 can also be used to prevent angiogenesis.

Example 4: Additive Effects on LPS-Activated Microglia-Induced Human Retinal Microvascular Endothelial Cells Tube Formation when Combining Laquinimod or ABR-215174 with an Angiogenesis Inhibitor, Such as Aflibercept, (Eylea®), as Compared to Monotherapies Microglia, especially activated microglia play important roles in angiogenesis and maintenance of vascular function haemostasis in the retinal microvasculature (Ding et al 2018). It is contemplated that a co-culture of human retinal microvasculature endothelial cells (HRMEC's) and human microglia from brain can be used to assess the effects of a compound of the disclosure, such as laquinimod, tasquinimod, ABR-215174 or ABR-215691, on neovascularization. A method such as the one outlined below may be used.

Methods

This study may be carried out substantially as outlined in Example 3.

Tube Formation Assay

Tube formation assay is performed using 24-well plate wells coated with Matrigel or in 96-wells as described Ding et al. 2018 (Ding et al. BMC Ophthalmology (2018) 18:249): A 96-well plate is coated with 50 μL/well Matrigel at 37° C. for 30 min. After co-culturing with microglia for 24 h, HRMECs are seeded on the Matrigel at $1.5 \times 10^4$ cells/well in 100 μL medium. After a period of time, for example 4 h, tube formation is observed and photographed with a microscope (Leica Microsystems). Images are analysed using the Angiotool plugin (Zudaire et al., 2011, PLoS one, 6, 11, e27385) for ImageJ (NIH public domain). Total tube area, tube length, density, lacunarity, and branching index (number of junctions and endpoints) are quantified.

Results and Conclusion

It is contemplated that when combining a compound of the disclosure, such as laquinimod 1 and 10 μM or ABR-2151740.01 and 0.1 μM, with Aflibercept (30 nM) a clear additive effect will be seen compared to each compound used as monotherapy.

The invention claimed is:

1. A method of treating an eye disease or eye disorder associated with excessive vascularization of the eye, wherein the eye disease or eye disorder is selected from corneal neovascularisation, neovascularisation of the iris, neovascularisation of the ciliary body, corneal pannus, choroidal neovascularisation, retinal neovascularisation, wet age-related macular degeneration, proliferative diabetic retinopathy, retinopathy of prematurity, and ischemic retinopathy, said method comprising administering a composition comprising a therapeutically effective amount of des-ethyl laquinimod having the structure:

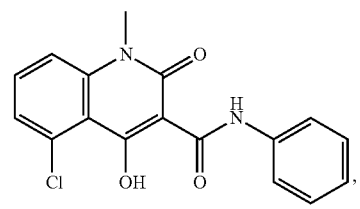

formula (IV)

or a pharmaceutically acceptable salt thereof, to a subject in need thereof, wherein the route of administration is topical or oral.

2. The method according to claim 1, wherein the eye disease or eye disorder is selected from corneal neovascularisation, neovascularisation of the iris, neovascularisation of the ciliary body, and corneal pannus.

3. The method according to claim 2, wherein the eye disease or eye disorder is corneal neovascularisation.

4. The method according to claim 1, wherein the eye disease or eye disorder is selected from proliferative diabetic retinopathy, retinopathy of prematurity, and ischemic retinopathy.

5. The method according to claim 4, wherein the eye disease or eye disorder is proliferative diabetic retinopathy.

6. The method according to claim 4, wherein the eye disease or eye disorder is retinopathy of prematurity.

7. The method according to claim 4, wherein the eye disease or eye disorder is ischemic retinopathy.

8. The method according to claim 1, wherein the eye disease or eye disorder is selected from choroidal neovascularisation, retinal neovascularisation, and wet age-related macular degeneration.

9. The method according to claim 8, wherein the eye disease or eye disorder is choroidal neovascularisation.

10. The method according to claim 8, wherein the eye disease or eye disorder is retinal neovascularisation.

11. The method according to claim 8, wherein the eye disease or eye disorder is wet age-related macular degeneration.

12. The method according to claim 1, wherein the composition comprises or is administered in combination with an angiogenesis inhibitor.

13. The method according to claim 1, wherein the composition comprises or is administered in combination with a VEGF inhibitor selected from aflibercept, ranibizumab, bevacizumab, brolucizumab, abicipar pegol, conbercept, and faricimab.

14. The method according to claim 1, wherein the composition comprises or is administered in combination with at least one pharmaceutically acceptable excipient.

15. The method according to claim 12, wherein the angiogenesis inhibitor is aflibercept.

* * * * *